(12) United States Patent
Park et al.

(10) Patent No.: US 10,723,760 B2
(45) Date of Patent: Jul. 28, 2020

(54) METHOD FOR PREPARING SITE-SPECIFICALLY MODIFIED PROTEIN BASED ON NOVEL CARBON-CARBON BOND FORMATION

(71) Applicant: Korea Advanced Institute of Science and Technology, Daejeon (KR)

(72) Inventors: Hee-Sung Park, Daejeon (KR); Hee-Yoon Lee, Daejeon (KR); Aerin Yang, Daejeon (KR); Sura Ha, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 125 days.

(21) Appl. No.: 15/692,403

(22) Filed: Aug. 31, 2017

(65) Prior Publication Data
US 2018/0066011 A1    Mar. 8, 2018

Related U.S. Application Data

(60) Provisional application No. 62/383,245, filed on Sep. 2, 2016.

(51) Int. Cl.
| | |
|---|---|
| *C07K 1/00* | (2006.01) |
| *C07K 1/13* | (2006.01) |
| *C07K 1/107* | (2006.01) |
| *C07K 2/00* | (2006.01) |

(52) U.S. Cl.
CPC ............ *C07K 1/006* (2013.01); *C07K 1/1077* (2013.01); *C07K 1/13* (2013.01); *C07K 2/00* (2013.01)

(58) Field of Classification Search
None
See application file for complete search history.

(56) References Cited

U.S. PATENT DOCUMENTS

| | | | | | |
|---|---|---|---|---|---|
| 2007/0249014 | A1* | 10/2007 | Agnew | ................ | A61K 47/549 435/68.1 |
| 2011/0144304 | A1* | 6/2011 | Bernardes | ................ | C07K 1/02 530/345 |
| 2014/0335561 | A1* | 11/2014 | Park | ........................ | C12P 21/00 435/68.1 |

FOREIGN PATENT DOCUMENTS

| | | |
|---|---|---|
| KR | 1020140133744 A | 11/2014 |
| KR | 10-2016-0053885 A | 5/2016 |

OTHER PUBLICATIONS

Lang, K., et al., "Cellular Incorporation of Unnatural Amino Acids and Bioorthogonal Labeling of Proteins", "Chemical Reviews", Mar. 21, 2014, pp. 4764-4806, vol. 114.
Lipshutz, B. H., et al., "C—C Bond Formation via Copper-Catalyzed Conjugate Addition Reactions to Enones in Water at Room Temperature", "Journal of the American Chemical Society", Dec. 12, 2012, pp. 19985-19988, vol. 134, No. 49.
Liu, C. C., et al., "Adding New Chemistries to the Genetic Code", "Annual Review of Biochemistry", Mar. 18, 2010, pp. 413-414, vol. 79.
Nguyen, D. P., et al., "Genetically Directing 3-N, N-Dimethyl-L-Lysine in Recombinant Histones", "Chemistry & Biology", Oct. 29, 2010, pp. 1072-1076, vol. 17.
Oda, Y., et al., "Enrichment analysis of phosphorylated proteins as a tool for probing the phosphoproteome", "Nature Biotechnology", Apr. 2001, pp. 379-382, vol. 19.
Postigo, A., et al., "Synthetically useful metal-mediated radical transformations in water and aqueous media", "Coordination Chemistry Reviews", Aug. 30, 2011, pp. 2991-3030, vol. 255.
Simon, M. D., et al., "The Site-Specific Installation of Methyl-Lysine Analogs into Recombinant Histones", "Cell", Mar. 9, 2007, pp. 1003-1012, vol. 128.
Van Kasteren, S. I., et al., "Expanding the diversity of chemical protein modification allows post-translational mimicry", "Nature", Apr. 26, 2007, pp. 1105-1109, vol. 446.
Vinogradova, E. V., et al., "Organometallic Palladium Reagents for Cysteine Bioconjugation", "Nature", Oct. 29, 2015, pp. 687-691, vol. 526, No. 7575.
Walsh, C. T., et al., "Protein Posttranslational Modifications: The Chemistry of Proteome Diversifications", "Angewandte Chemie International Edition", Dec. 1, 2005, pp. 7342-7372, vol. 44, No. 45.
Lee, S., et al., "A Facile Strategy for Selective Incorporation of Phosphoserine into Histones", "Angewandte Chemie Int. Ed.", 2013, pp. 5771-5775, vol. 52, Publisher: Wiley Online Library.
Degrado, S.J., et al., "Efficient Cu-Catalyzed Asymmetric Conjugate Additions of Alkylzincs to Trisubstituted Cyclic Enones", "J. Am. Chem. Soc.", 2002, pp. 13362-13363, vol. 124.
Knochel, P., et al., "Transmetalation Reactions Producing Organocopper Reagents", "Modern Organocopper Chemistry", 2002, pp. 1-34.
Wipf, P., et al., "Transmetalation Reactions of Alkylzirconocenes: Copper-Catalyzed Conjugate Addition to Enones", "J. Org. Chem.", 1991, pp. 6494-6496, vol. 56.

* cited by examiner

*Primary Examiner* — Iqbal H Chowdhury
(74) *Attorney, Agent, or Firm* — Hultquist, PLLC; Steven J. Hultquist

(57) ABSTRACT

A method for producing a site-specifically modified protein based on new carbon-carbon bond formation is disclosed, including the following three steps (marking, activation, and coupling steps): (a) marking of the modification site by incorporating a specific amino acid into a selected position of a target protein; (b) activation of the marked site; and (c) coupling of various post-translational modification (PTM) moieties or other chemical groups onto the activated site to obtain a site-specifically modified protein. The method for producing a site-specifically modified protein can incorporate desired diverse chemical groups including post-translational modification (PTM) moieties into a designated site in a target protein through a new carbon-carbon bond. Furthermore, the modified protein having a site-specific PTM exhibits the same chemical and functional properties as that of a target protein present in cells. Thus, the present invention is useful for studies of cellular proteins, human diseases including cancers and neurodegenerative diseases, and new drug discovery.

4 Claims, 23 Drawing Sheets
(14 of 23 Drawing Sheet(s) Filed in Color)
Specification includes a Sequence Listing.

Zn powder

\- 0.2 0.4 0.6 1 mg

Zn particle powder dust nano

CB

WB

SEQUENCE LISTING

```
<160> NUMBER OF SEQ ID NOS: 3

<210> SEQ ID NO 1
<211> LENGTH: 537
<212> TYPE: PRT
<213> ORGANISM: Artificial Sequence
<220> FEATURE:
<223> OTHER INFORMATION: SepRS mutant

<400> SEQUENCE: 1

Met Phe Lys Arg Glu Glu Ile Ile Glu Met Ala Asn Lys Asp Phe Glu
1               5                   10                  15

Lys Ala Trp Ile Glu Thr Lys Asp Leu Ile Lys Ala Lys Lys Ile Asn
            20                  25                  30

Glu Ser Tyr Pro Arg Ile Lys Pro Val Phe Gly Lys Thr His Pro Val
        35                  40                  45

Asn Asp Thr Ile Glu Asn Leu Arg Gln Ala Tyr Leu Arg Met Gly Phe
    50                  55                  60

Glu Glu Tyr Ile Asn Pro Val Ile Val Asp Glu Arg Asp Ile Tyr Lys
65                  70                  75                  80

Gln Phe Gly Pro Glu Ala Met Ala Val Leu Asp Arg Cys Phe Tyr Leu
                85                  90                  95

Ala Gly Leu Pro Arg Pro Asp Val Gly Leu Ser Asp Glu Lys Ile Ser
            100                 105                 110

Gln Ile Glu Lys Leu Gly Ile Lys Val Ser Glu His Lys Glu Ser Leu
        115                 120                 125

Gln Lys Ile Leu His Gly Tyr Lys Lys Gly Thr Leu Asp Gly Asp Asp
    130                 135                 140

Leu Val Leu Glu Ile Ser Asn Ala Leu Glu Ile Ser Ser Glu Met Gly
145                 150                 155                 160

Leu Lys Ile Leu Glu Asp Val Phe Pro Glu Phe Lys Asp Leu Thr Ala
                165                 170                 175
```

```
Val Ser Ser Lys Leu Thr Leu Arg Ser His Met Thr Ser Gly Trp Phe
            180                 185                 190

Leu Thr Val Ser Asp Leu Met Asn Lys Lys Pro Leu Pro Phe Lys Leu
            195                 200                 205

Phe Ser Ile Asp Arg Cys Phe Arg Arg Glu Gln Lys Glu Asp Lys Ser
            210                 215                 220

His Leu Met Thr Tyr His Ser Ala Ser Cys Ala Ile Ala Gly Glu Gly
225                 230                 235                 240

Val Asp Ile Asn Asp Gly Lys Ala Ile Ala Glu Gly Leu Leu Ser Gln
            245                 250                 255

Phe Gly Phe Thr Asn Phe Glu Phe Ile Pro Asp Glu Lys Lys Ser Lys
            260                 265                 270

Tyr Tyr Thr Pro Glu Thr Gln Thr Glu Val Tyr Ala Tyr His Pro Lys
            275                 280                 285

Leu Lys Glu Trp Leu Glu Val Ala Thr Phe Gly Val Tyr Ser Pro Val
            290                 295                 300

Ala Leu Ser Lys Tyr Gly Ile Asp Val Pro Val Met Asn Leu Gly Leu
305                 310                 315                 320

Gly Val Glu Arg Leu Ala Met Ile Ser Gly Asn Phe Ala Asp Val Arg
            325                 330                 335

Glu Met Val Tyr Pro Gln Phe Tyr Glu His Glu Leu Asn Asp Arg Asp
            340                 345                 350

Val Ala Ser Met Val Lys Leu Asp Lys Val Pro Val Met Asp Glu Ile
            355                 360                 365

Tyr Asp Leu Thr Lys Glu Leu Ile Glu Ser Cys Val Lys Asn Lys Asp
370                 375                 380

Leu Lys Ser Pro Cys Glu Leu Ala Ile Glu Lys Thr Phe Ser Phe Gly
385                 390                 395                 400

Lys Thr Lys Lys Asn Val Lys Ile Asn Ile Phe Ser Lys Ile Glu Gly
            405                 410                 415

Lys Asn Leu Leu Gly Pro Ser Ile Leu Asn Glu Ile Tyr Val Tyr Asp
            420                 425                 430

Gly Asn Val Ile Gly Ile Pro Glu Ser Phe Asp Gly Val Lys Glu Glu
            435                 440                 445

Phe Lys Asp Phe Leu Glu Lys Gly Lys Ser Glu Gly Val Ala Thr Gly
            450                 455                 460

Ile Arg Tyr Ile Asp Ala Leu Cys Phe Lys Ile Thr Ser Lys Leu Glu
465                 470                 475                 480

Glu Ala Phe Val Ser Asn Thr Thr Glu Phe Lys Val Lys Val Arg Arg
            485                 490                 495

Val Arg Ser Leu Ser Asp Ile Asn Leu Lys Ile Asp Asp Ile Ala Ile
            500                 505                 510

Lys Gln Ile Met Ser Lys Asn Lys Val Ile Asp Val Arg Gly Pro Val
            515                 520                 525

Phe Leu Asn Val Glu Val Lys Ile Glu
        530                 535

<210> SEQ ID NO 2
<211> LENGTH: 394
<212> TYPE: PRT
<213> ORGANISM: Artificial Sequence
<220> FEATURE:
<223> OTHER INFORMATION: EF-Tu Mutant
```

<400> SEQUENCE: 2

```
Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Val Gly Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Ser
385                 390
```

```
<210> SEQ ID NO 3
<211> LENGTH: 75
<212> TYPE: RNA
<213> ORGANISM: Artificial Sequence
<220> FEATURE:
<223> OTHER INFORMATION: tRNA-Sep

<400> SEQUENCE: 3
gccgggguag ucuagggguu aggcagcgga cucuagaucc gccuuacgug gguucaaauc    60 ccaccccgg cucca                                                      75
```

METHOD FOR PREPARING SITE-SPECIFICALLY MODIFIED PROTEIN BASED ON NOVEL CARBON-CARBON BOND FORMATION

CROSS-REFERENCE TO RELATED APPLICATIONS

This application claims the benefit under 35 U.S.C. 119 of U.S. Provisional Patent Application No. 62/383,245 filed Sep. 2, 2016. The disclosure of such U.S. Provisional Patent Application No. 62/383,245 is hereby incorporated herein by reference in its entirety, for all purposes.

TECHNICAL FIELD

The present invention relates to a method for producing a site-specifically modified protein based on new carbon-carbon bond formation, the method comprising the following three steps (marking, activation, and coupling steps): (a) marking of the modification site by incorporating a specific amino acid into a selected position of a target protein; (b) activating of the marked site; and (c) coupling of chemical groups including post-translational modification (PTM) moieties onto the activated site to obtain a site-specifically modified protein.

BACKGROUND ART

Posttranslational modifications (PTMs) play vital roles in expanding protein functional diversity and critically affect numerous biological processes (C T Walsh et al., Angew. Chem. Int. Ed. Engl. Vol. 44 pp. 7342-72, 2005). The availability of proteins with specific modifications at selected residues is essential for experimental strategies to investigate fundamental biological mechanisms. Methods to generate diverse native protein covalent modifications currently do not exist.

Genetic code expansion approaches are useful in producing recombinant proteins with specific modifications (K. Lang et al., Chem. Rev. Vol. 114, pp. 4764-4806, 2014; C C Liu et al., Annu. Rev. Biochem. Vol. 79, pp. 413-44, 2010), but rely on the availability of an orthogonal tRNA/tRNA synthetase pair for acylation of a specific non-canonical amino acid. Despite much technical progress, the creation of many important protein modifications (e.g., trimethyl lysine) is not yet feasible.

Cys-based strategies have been widely applied to generate protein conjugates or mimics of PTMs (E. V. Vinogradova et al., Nature. Vol. 526, pp. 687-691, 2015; M. D. Simon et al., Cell. Vol. 128. pp. 1003-1012, 2007; S, I. van Kasteren et al., Nature. Vol. 446, pp. 1105-09, 2007). However, the final products produced by such methods are PTM analogs whose value for searching out unidentified properties of the natural system may still be questionable (D. P. Nguyen et al, Chem. Biol. Vol. 17, pp. 1072-76, 2010).

Thus, despite such extensive efforts, synthetic approaches for many authentic PTMs are not available, as no C—C bond forming reactions have been successfully applied to protein modifications despite the prevalence of such reactions in organic chemistry.

The present inventors have developed a method of producing a site-specifically phosphorylated protein by use of a SepRS variant and an EF-Tu variant (U.S. Pat. No. 9,322,044, Korean Patent Application No. 10-2016-0053885). Still, this method has a limitation in that it enables only selective phosphorylation among many PTMs present in intracellular proteins.

Meanwhile, phosphoamino acids are known to be labile under alkaline conditions (Y. Oda et al., Nat. Bioechnol. Vol. 19, pp. 379-82, 2001).

Also, reactions that form carbon-carbon bonds using transition metals as catalysts for generation of diverse organic compounds have been reported in recent years (A. Postigo et al., Chem. Rev. Vol. 255. pp. 2991-3030, 2001; B. H. Lipshutz et al., J. Am. Chem. Soc. Vol. 134. pp. 19985-88, 2012).

Under this background, the present inventors have made extensive efforts to produce a site-specifically modified protein via new carbon-carbon bond formation for the first time. As a result, the inventors have found that, when a specific site in a target protein is marked with a phosphorylated amino acid, is activated under alkaline conditions, and then is conjugated with an organic halogen compound containing a desired modification moiety or chemical group in the presence of a transition metal under optimized reaction condition, a site-specifically modified protein having the same chemical and functional properties as that of authentic PTMs present in cells can be produced, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

An object of the present invention is to provide a method for producing a site-specifically modified protein via new carbon-carbon bond formation.

Another object of the present invention is to provide a reagent composition for coupling of chemical groups including post-translational modification moieties onto a target protein, the composition comprising an organic halogen compound, a transition metal, and other auxiliary reagents.

Still another object of the present invention is to provide a kit for producing a site-specifically modified target protein.

Yet another object of the present invention is to provide the use of a reagent composition for coupling of diverse chemical groups including post-translational modification moieties onto a specific position of a target protein the composition comprising an organic halogen compound, a transition metal, and other auxiliary reagents.

Technical Solution

To achieve the above objects, the present invention provides a method for producing a site-specifically modified protein based on new carbon-carbon bond formation, the method comprising the following three steps: (a) marking of the modification site by incorporating a specific amino acid into a selected position of a target protein; (b) activating the marked site; and (c) coupling of various post-translational modification (PTM) moieties and other chemical groups onto the activated site to obtain a modified protein.

The present invention also provides a method for producing a site-specifically and authentically PTM-modified target protein, comprising the steps of: (a) incorporating phosphoserine (Sep) into a specific site in a target protein (marking step); (b) treating the phosphoserine-incorporated target protein with an alkali to convert the phosphoserine to dehydroalanine (Dha) to thereby activate the modification site (activation step); and (c) coupling the Dha-containing protein with an organic halogen compound containing various post-translational modification (PTM) moieties in the presence of a transition metal catalyst under optimized reaction condition to generate a carbon-carbon bond between the Dha and the alkyl radical (coupling step), thereby obtaining a site-specifically PTM-modified protein The present invention also provides a method for producing a target protein which is modified with diverse chemical and functional groups at a specific site, comprising the steps of: (a) incorporating phosphoserine (Sep) into a specific site in a target protein(marking step); (b) treating the phosphoserine-incorporated target protein with an alkali to convert the phosphoserine to dehydroalanine (Dha) to thereby activate the modification site (activation step); and (c) coupling the Dha-containing protein with an organic halogen compound containing diverse chemical and functional groups in the presence of a transition metal catalyst under optimized reaction condition to generate a carbon-carbon bond between the Dha and the alkyl radical (coupling step), thereby obtaining a protein with selective chemical modifications.

The present invention also provides a reagent composition for coupling of various post-translational modification (PTM) moieties or other chemical and functional groups onto a specific position of a target protein, the composition comprising an organic halogen compound, a transition metal, and other auxiliary reagents including buffer and surfactant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIGS. 4, 1 to 5 is alkyl iodides for producing PTM moieties, 13 is an alkyl iodide for connecting fluorescent dye, and 6 to 12 are commercialized products.

FIG. 5 shows the results of MALDI-TOF MS analysis of proteins produced according to the method of the present invention, in which lysine at residue 79 of histone H3 is formylated (upper panel) and alkylated (lower panel).

BEST MODE FOR CARRYING OUT THE INVENTION

Figure 1A:
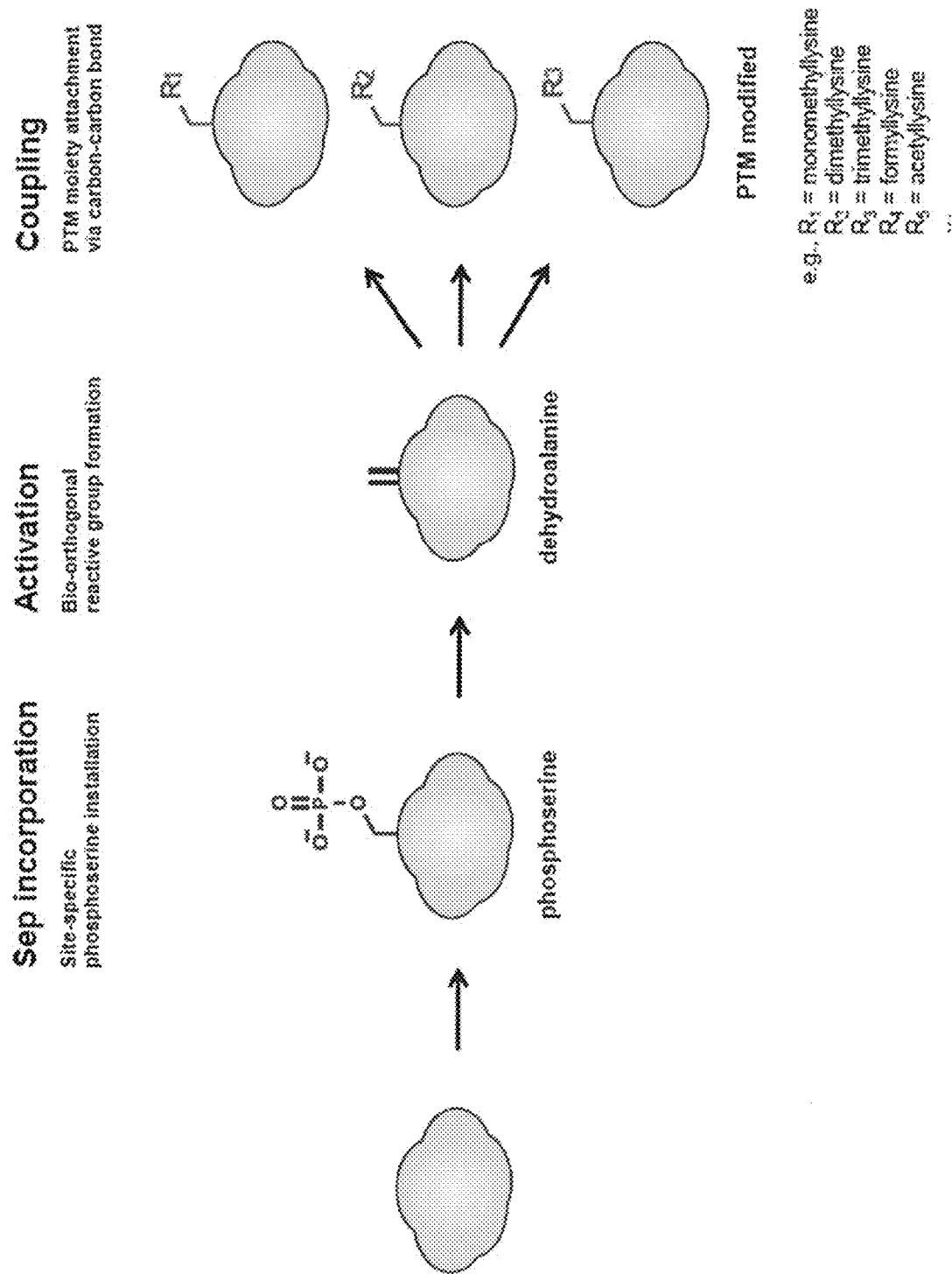
FIG. 1A is a schematic view showing a 3-step process according to the present invention.
Figure 1B:
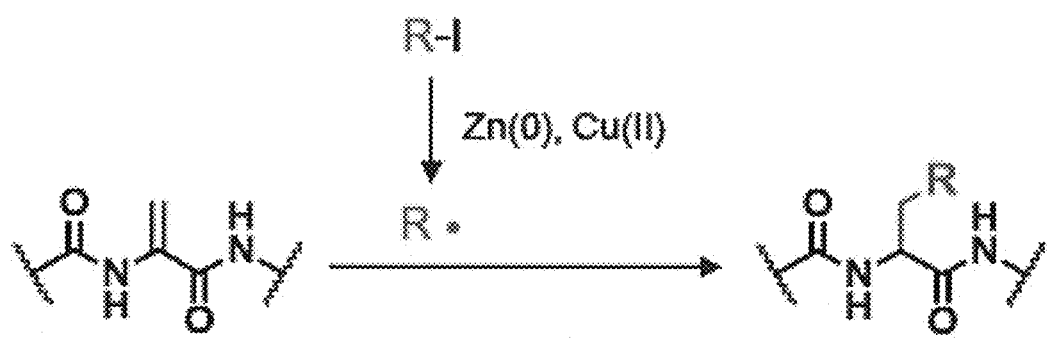
FIG. 1B is a schematic view showing a new coupling scheme enabling carbon-carbon bond formation in proteins, which is used in the third step of the method according to the present invention.

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, whether a chemical modification can be coupled to a desired site in a target protein by new carbon-carbon bond formation was examined.

In the present invention, the following steps were performed: incorporating a specific amino acid into a desired site in a target protein; activating the specific amino acid; and conjugating the activated amino acid with compounds containing various post-translational modification (PTM)

moieties or diverse chemical and functional groups in the presence of a transition metal catalyst under optimized reaction condition to the desired site of the target protein. As a result, it was found that various PTM moieties and diverse chemical groups could be coupled to the desired site of the target protein via new carbon-carbon bond.

Specifically, in one example of the present invention, phosphoserine (Sep) was incorporated into position 79 of histone H3, thereby preparing histone H3Sep79. Then, based on the fact that phosphoamino acids are labile under alkaline conditions, treatment with an alkaline solution was performed to convert the Sep to dehydroalanine (Dha). The Dha was treated with a transition metal catalyst (Zn or Cu), and reacted with alkyl iodides containing PTM moieties under optimized conditions, thereby obtaining modified proteins in which desired authentic PTMs (for example, mono-, di-, and tri-methylation of Lys) are generated at position 79 of histone H3 (FIGS. 1A-1B and FIGS. 2A-2C). It was seen that the modified proteins would function in the same manner as actual in vivo modified proteins as demonstrated by in vitro transcription assay (FIGS. 3A-3D).

Therefore, in one aspect, the present invention is directed to a method for producing a site-specifically modified protein, the method comprising the following three steps: (a) marking of the modification site by incorporating a specific amino acid into a selected position of a target protein; (b) activation of the marked site; and (c) coupling of various post-translational modification (PTM) moieties onto the activated site to obtain an authentically modified protein.

As used herein, the term "post-translational modification (PTM)" means that a specific chemical group is attached to the side chain of an amino acid synthesized after protein synthesis (a step in which mRNA transcribed from DNA is translated into an amino acid primary chain). The term is used in the same sense as the term "protein modification".

In the present invention, the post-translational modification moiety can be used without any limitation as long as it is a PTM moiety of a protein that is generally well-known, and may be preferably produced by at least one reaction selected from the group consisting of acylation, acetylation, mono-methylation, di-methylation, tri-methylation, amidation, butyrylation, carboxylation, glycosylation, formylation, hydroxylation, iodination, oxidation, phosphorylation, propionylation, succinylation, sulfation, glycation, carbonylation, formylation, ubiquitination, sumoylation, neddylation, nitrosylation, lipidation, biotinylation, pegylation, and pupylation, but is not limited thereto.

Figure 4:
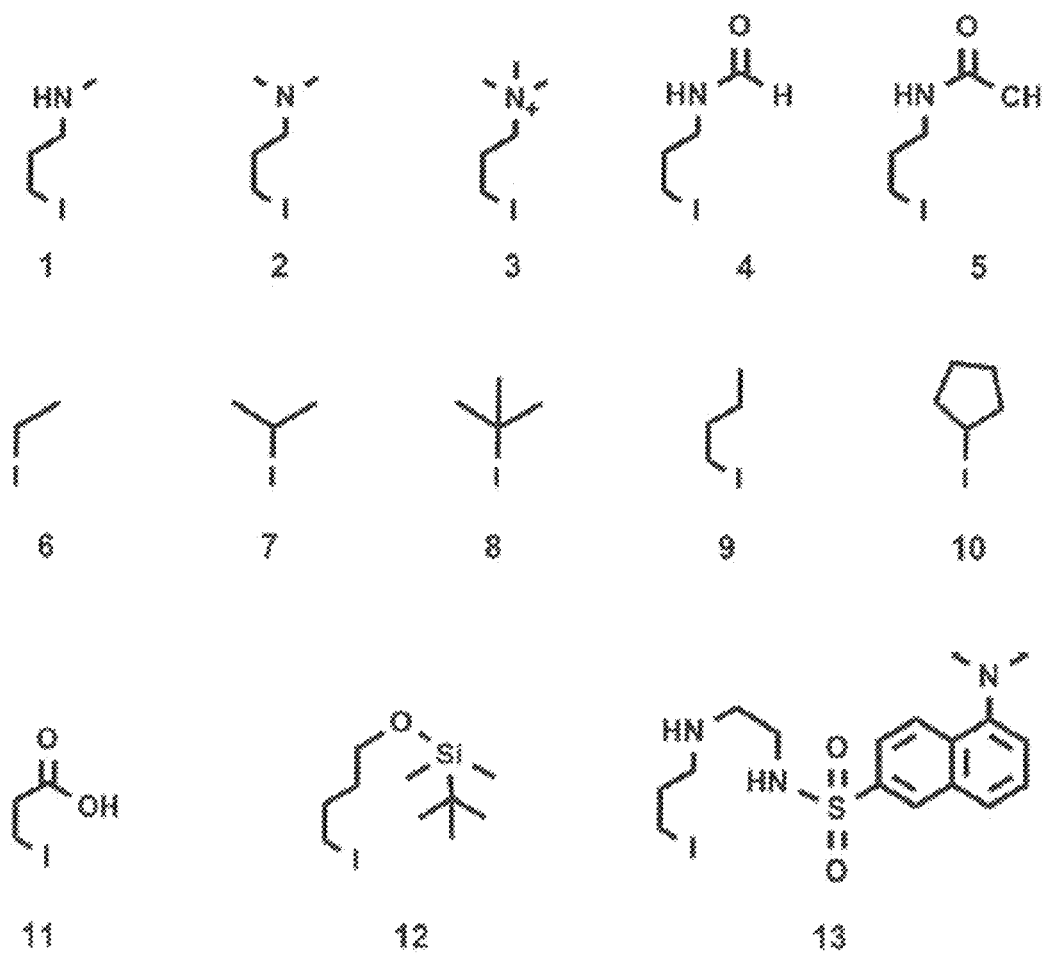
FIG. 4 shows the chemical structures of alkyl iodides used in the present invention.

In the present invention, various organic halogen compounds with diverse chemical and function groups, including 3-iodo-N-methylpropan-1-amine hydrochloride, 3-iodo-N—N-dimethylpropan-1-amine hydrochloride, 3-iodo-N—N—N-trimethylpropan-1-amine hydrochloride, N-(3-iodopropyl)formamide, N-(3-Iodopropyl)acetamide), 5-(dimethylamino)-N-(2-((3-iodopropyl)amino)ethyl)naphtalene-1-sulfonamide hydrochloride), iodobutane, 2-iodopropane, 2-iodo-2-methylpropane, 1-iodobutane, iodocyclopentane, 3-iodopropionic acid, and tert-butyl(4-iodobutoxy) dimethylsilane (1st to 13th compounds in FIG. 4) can be coupled to the Dha-containing protein through a new carbon-carbon bond formation, but is not limited thereto. Any alkyl compound can be used without limitation as long as it is attached to halide.

In the present invention, the amino acid that is incorporated in step (a) can be used without any limitation as long as it is an amino acid having a reactive moiety that can be activated by a chemical reaction. The amino acid may be preferably a non-natural amino acid, most preferably phosphoserine (Sep), but is not limited thereto.

In the present invention, the method of incorporating Sep can be used without any limitation as long as it is a method capable of incorporating Sep into the specific site of the target protein. Preferably, the method of incorporating Sep may be a method disclosed in U.S. Pat. No. 9,322,044, Korean Patent Application No. 10-2016-0052369, and more preferably comprise a step of expressing an mRNA encoding the target protein by use of $tRNA^{Sep}$ that recognizes at least one codon in the mRNA of the target protein, an O-phosphoseryl-tRNA synthetase (SepRS) variant for aminoacylating the $tRNA^{Sep}$ with phosphoserine (Sep), and an elongation factor Tu (EF-Tu) variant that protects a complex of the $tRNA^{Sep}$ and the SepRS from deacylation, but is not limited thereto.

In the present invention, the SepRS variant may comprise an amino acid sequence represented by SEQ ID NO: 1, and the EF-Tu variant may comprise an amino acid sequence represented by SEQ ID NO: 2.

In the present invention, the $tRNA^{Sep}$ may comprise an amino acid sequence represented by SEQ ID NO: 3.

In the present invention, step (b) may be performed using any method capable of activating the residue marked by a specific amino acid. Preferably, step (b) may comprise removing a special chemical group from the marked residue to generate activated chemical structure (dehydroalanine, Dha) for carbon-carbon forming conjugation reaction.

In the present invention, the special chemical group of the marked residue may be a phosphate group.

Specifically, in the present invention, a phosphate-containing specific amino acid (phosphoserine, Sep) is incorporated into the specific site of the target protein. Then, based on the fact that phosphoamino acids are labile under alkaline conditions, treatment with an alkali is performed to convert the phosphate group to dehydroalanine.

In the present invention, the removal of the special chemical group and generation of dehydroalanine may be performed by treatment with an alkali or a catalyst, for example a chemical catalyst compound or an enzyme but is not limited thereto.

In the present invention, the alkali can be used without any limitation as long as it is a compound that releases OH ions in an aqueous solution, but the alkali may preferably be selected from the group consisting of lithium hydroxide (LiOH), barium hydroxide ($Ba(OH)_2$), strontium hydroxide ($Sr(OH)_2$), magnesium hydroxide ($Mg(OH)_2$), calcium hydroxide ($Ca(OH)_2$), radium hydroxide ($Ra(OH)_2$), and beryllium hydroxide ($Be(OH)_2$).

In the present invention, the coupling of the post-translational modification moiety in step (c) may be performed by conjugation between an organic halogen compound and the activated residue (dehydroalanine, Dha) through carbon-carbon bond forming reaction in the presence of a transition metal under optimized reaction condition.

The converted dehydroalanine has an alkene moiety, and thus can act as a radical acceptor. Using a water-based transmetalation reaction, an organic halogen compound containing a desired post-translational modification (PTM) moiety is converted by a transition metal catalyst into a reactive alkyl radical, which is then conjugated to the radical acceptor Dha under optimized reaction condition, thereby generating a PTM-modified protein at a designated residue through a new carbon-carbon bond.

In the present invention, the conditions of the carbon-carbon bond formation may be changed depending on the characteristics of a target protein, and the carbon-carbon bond formation may be performed at pH 4.0-5.0 if the target protein is histone.

In the present invention, the transition metal may be selected from the group consisting of zinc, copper, iron, gold, silver, mercury, cobalt, manganese, and nickel.

In the present invention, any organic halogen compound containing post-translational modification moieties or other chemical groups can be used without any limitation as long as it is a compound whose moiety can be modified into a radical by transmetalation. Preferably, the post-translational modification moiety may be a compound represented by the following formula 1:

R—X　　　　　　　　　　　　　　　　　　　Formula 1 wherein R is an alkyl group, a cycloalkyl group, a $C_2$-$C_6$ alkenyl group, a $C_2$-$C_6$ alkynyl group, an alkoxy group, a $C_1$-$C_6$ alkylsulfonyl group, a $C_1$-$C_6$ alkylcarbonyl group, a $C_1$-$C_6$ alkoxycarbonyl group, a $C_3$-$C_6$ cycloalkylcarbonyl group, a carboxy group, a hydrocarbonyl group, an amino group, an alkylamino group, an arylamino group, an alkoxycarbonylamino group, an aryloxycarbonylamino group, a hydrocarbonylamino group, an alkylcarbonylamino group, an arylcarbonylamino group, an alkylthio group, an arylthio group, a cyano group (wherein the alkyl group is $C_1$-$C_6$, the alkoxy group is $C_1$-$C_6$, and the aryl group is $C_6$-$C_{14}$), a phosphoryl group, a succinyl group, a formyl group, an acyl group, a ubiquitin group, an SUMO protein, or an NEDD protein, and wherein X is a halogen.

In the present invention, the compound may be selected from the group consisting of 3-Iodo-N-methylpropan-1-amine hydrochloride, 3-Iodo-N—N-dimethylpropan-1-amine hydrochloride, 3-Iodo-N—N—N-trimethylpropan-1-amine hydrochloride, N-(3-iodopropyl)formamide, N-(3-Iodopropyl)acetamide), 5-(dimethylamino)-N-(2-((3-iodopropyl)amino)ethyl)naphtalene-1-sulfonamide hydrochloride), iodobutane, 2-iodopropane, 2-iodo-2-methylpropane, 1-iodobutane, iodocyclopentane, 3-iodopropionic acid, and tert-butyl(4-iodobutoxy)dimethylsilane, but is not limited thereto.

In the present invention, the halogen may be selected from the group consisting of fluorine, chlorine, bromine, and iodine, but is not limited thereto.

Figure 2A:
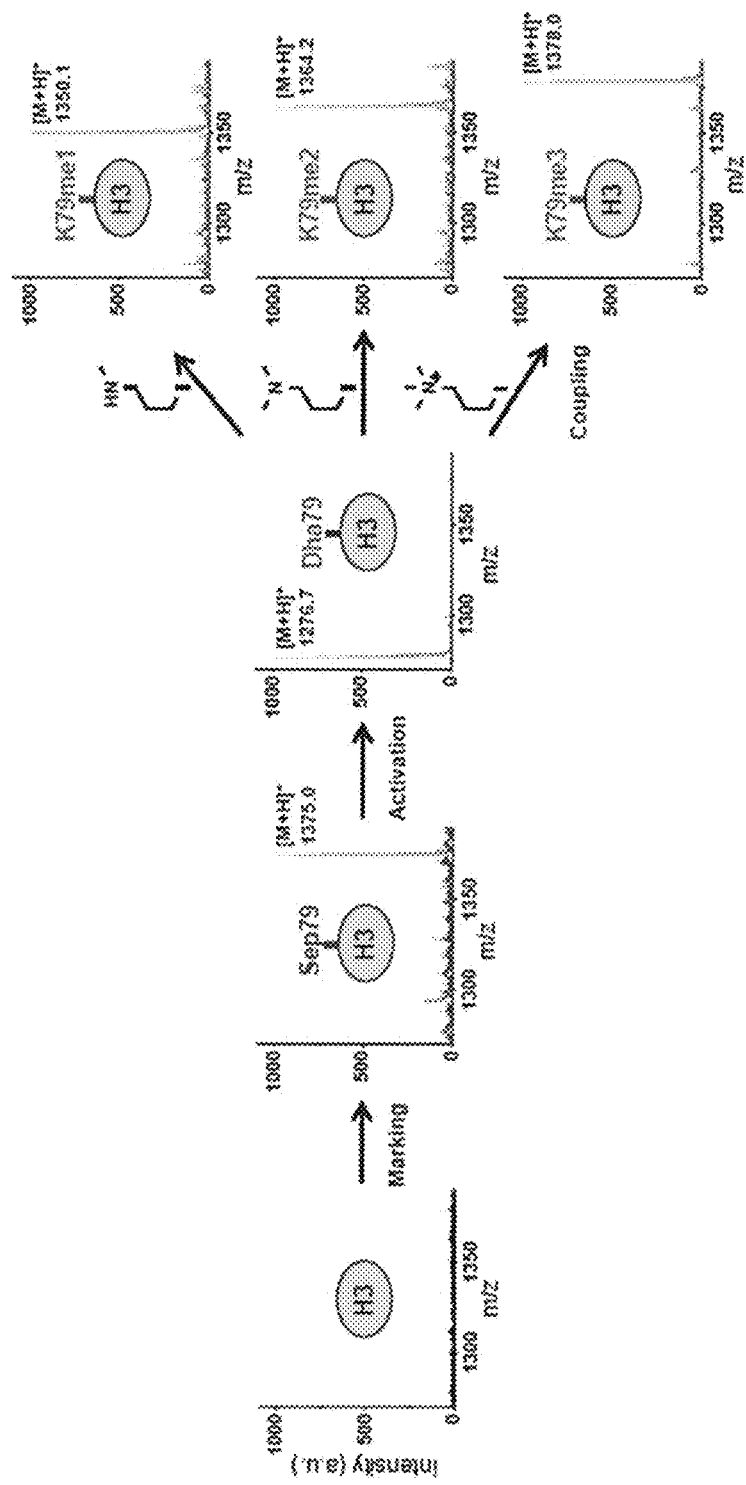
FIG. 2A shows MALDI-TOF analysis results indicating that residue 79 of histone H3 was methylated according to the method of the present invention.
Figure 2B:
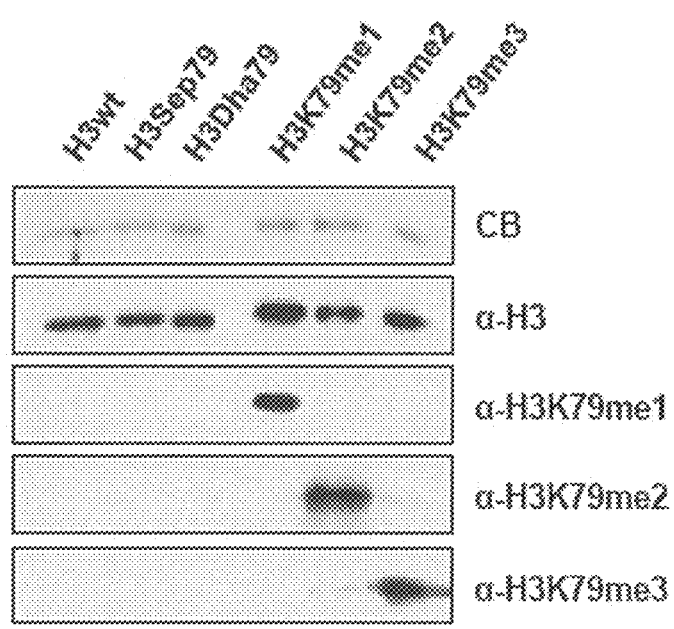
FIG. 2B shows Western blot analysis results indicating detection of the modified proteins shown in FIG. 1A.
Figure 2C:
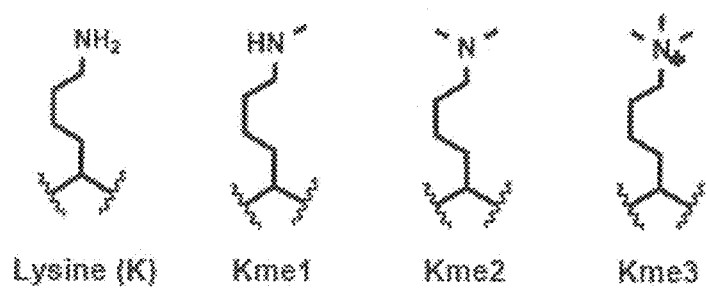
FIG. 2C shows the chemical structures of lysine and differentially methylated lysine residues (modified with monomethyl, dimethyl, and trimethyl).

In one example of the present invention, X. Laevis histone H3 mRNA, containing UAG at the position of a codon coding for an amino acid at position 79 and also comprising $His_6$-Tag at the C-terminus, was expressed in an E. coli strain containing SepRS9 and EF-Sep21, thereby producing a histone H3Sep79 protein. Next, the protein was treated with LiOH, Ba(OH)$_2$ or Sr(OH)$_2$ under different conditions to obtain histone H3 Dha79. Then, the histone H3 Dha79 was treated in sodium acetate buffer (pH 4.5) with trimethyl iodide (3-iodo-NmNmN-trimethylpropan-1-amine), zinc powder, Cu(OAc)$_2$, Triton X-100 and TMEDA, thereby producing histone H3 K79me3 (FIGS. 2A-2C).

Therefore, in another aspect, the present invention is directed to a method for producing a site-specifically and authentically modified target protein via new carbon-carbon bond formation, comprising the steps of: (a) incorporating phosphoserine (Sep) into a specific site in a target protein; (b) treating the phosphoserine-incorporated target protein with an alkali to convert the phosphoserine to dehydroalanine (Dha) to thereby activate the target protein; and (c) coupling the Dha with an organic halogen compound containing a post-translational modification (PTM) moiety by forming a carbon-carbon bond in the presence of a transition metal catalyst under optimized reaction condition, thereby obtaining a site-specifically and authentically PTM-modified protein.

In the present invention, the alkali can be used without any limitation as long as it is a compound that emits OH-ions in an aqueous solution, but the alkali may preferably be selected from the group consisting of lithium hydroxide (LiOH), barium hydroxide (Ba(OH)$_2$), strontium hydroxide (Sr(OH)$_2$), magnesium hydroxide (Mg(OH)$_2$), calcium hydroxide (Ca(OH)$_2$), radium hydroxide (Ra(OH)$_2$), and beryllium hydroxide (Be(OH)$_2$).

In the present invention, the transition metal may be selected from the group consisting of zinc, copper, iron, gold, silver, mercury, cobalt, manganese, and nickel.

The present invention is also directed to a reagent composition for coupling a post-translational modification (PTM) moiety to a target protein, the composition comprising an organic halogen compound, a transition metal, and other auxiliary reagents.

In the present invention, the organic halogen compound may be selected from the group consisting of 3-Iodo-N-methylpropan-1-amine hydrochloride, 3-Iodo-N—N-dimethylpropan-1-amine hydrochloride, 3-Iodo-N—N—N-trimethylpropan-1-amine hydrochloride, N-(3-iodopropyl) formamide, N-(3-Iodopropyl)acetamide), 5-(dimethylamino)-N-(2-((3-iodopropyl)amino)ethyl)naphtalene-1-sulfonamide hydrochloride), iodobutane, 2-iodopropane, 2-iodo-2-methylpropane, 1-iodobutane, iodocyclopentane, 3-iodopropionic acid, and tert-butyl(4-iodobutoxy) dimethylsilane, but is not limited thereto.

In the present invention, the transition metal may be selected from the group consisting of zinc, copper, iron, gold, silver, mercury, cobalt, manganese, and nickel, but is not limited thereto.

In the present invention, the reagent composition may further comprise a surfactant, and the surfactant may be selected from Triton X-100, TPGS, Tween20, Tween80, IGEPAL, and Brij35, but is not limited thereto.

In the present invention, the reagent composition may further comprise TMEDA.

In the present invention, the reagent composition may further comprise various buffers including sodium acetate, sodium citrate, and ammonium acetate, but is not limited thereto.

In the present invention, the reagent composition may comprise an alkyl iodide, zinc powder, Cu(OAc)$_2$, Triton X-100, TMEDA, and Sodium acetate when the target protein is histone and the PTM moiety to be coupled is produced by methylation.

Figure 5:
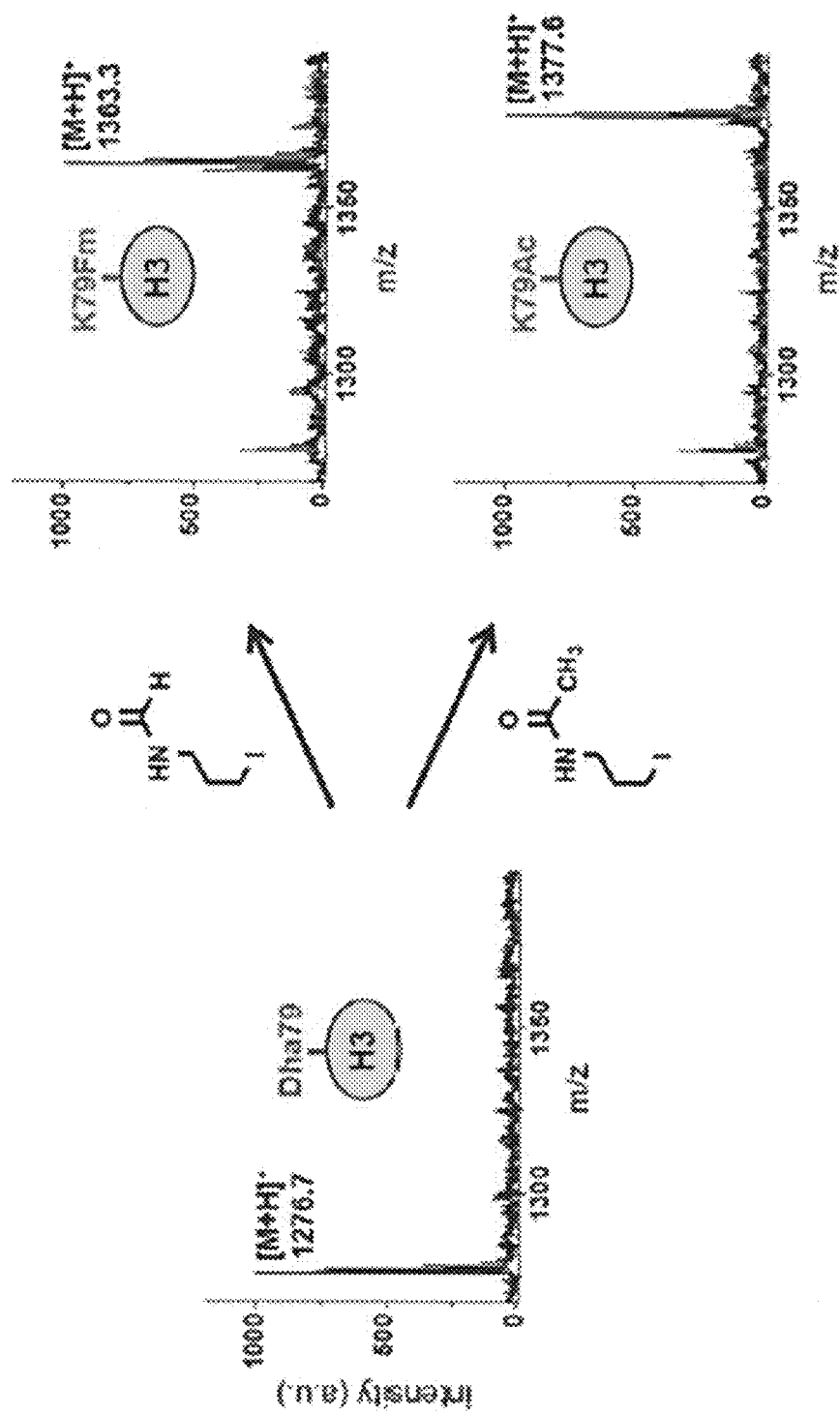
Figure 6:
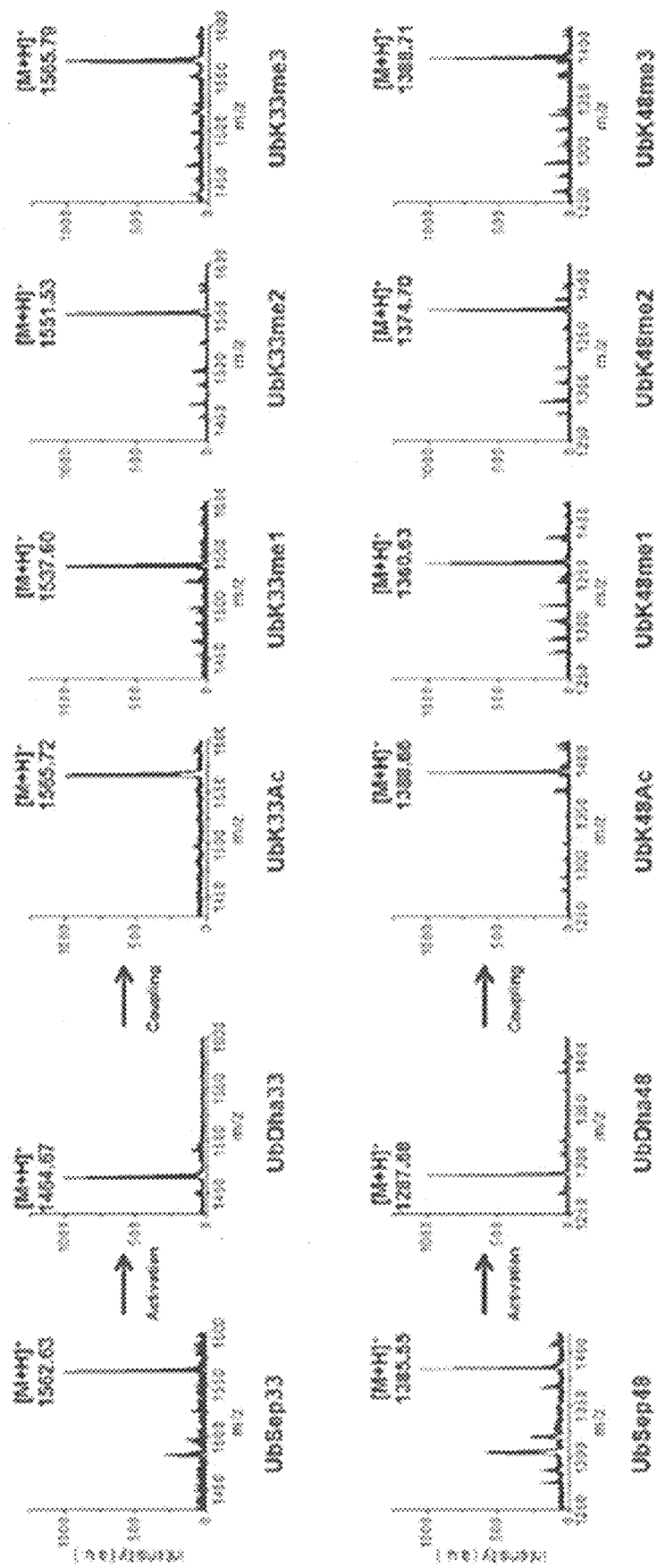
FIG. 6 shows the results of MALDI-TOF MS analysis of proteins with ubiquitylated lysine modifications (acetylation and various methylations, produced according to the method of the present invention.
Figure 7:
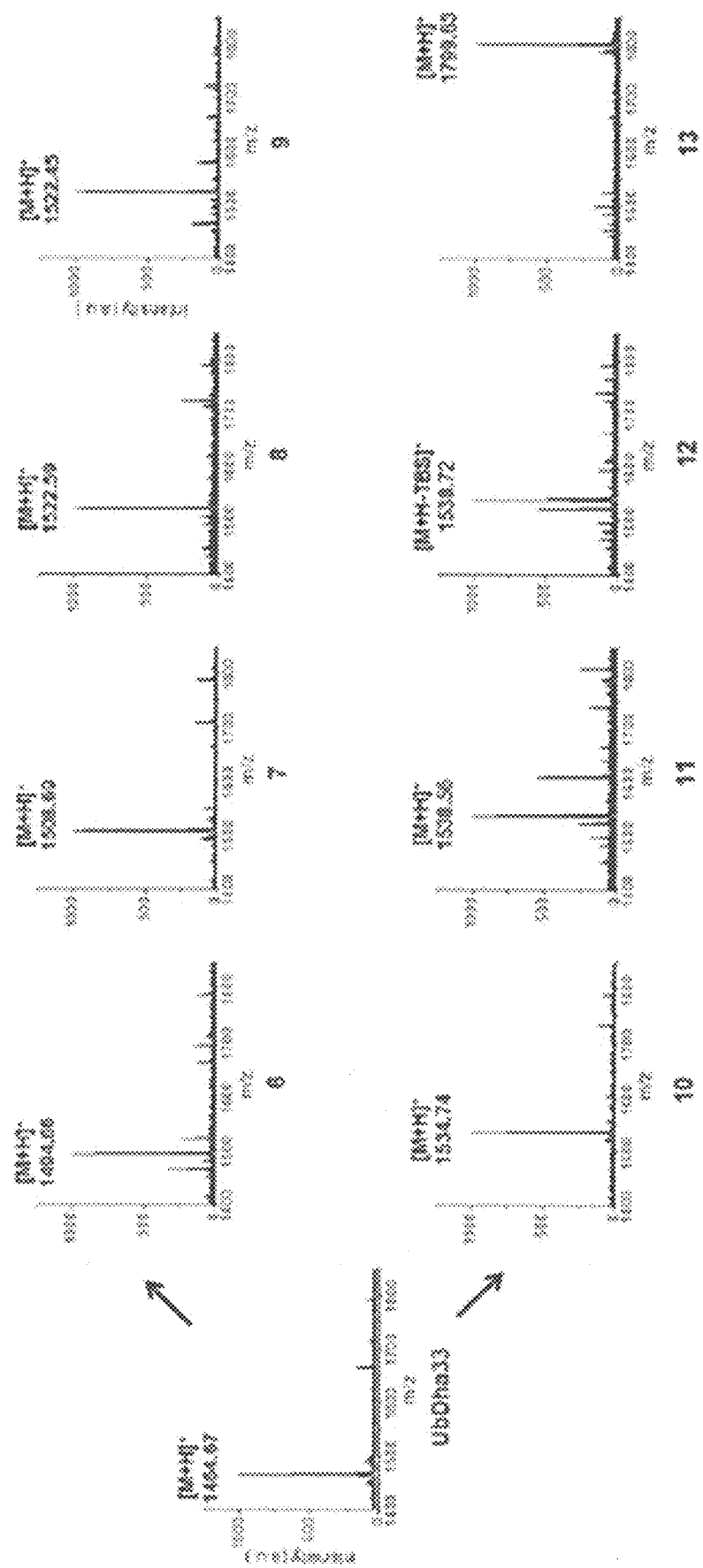
FIG. 7 shows the results of MALDI-TOF MS analysis of proteins produced by coupling commercial product modifications (6 to 12 in FIG. 4) to position 33 according to the method of the present invention.
Figure 8:
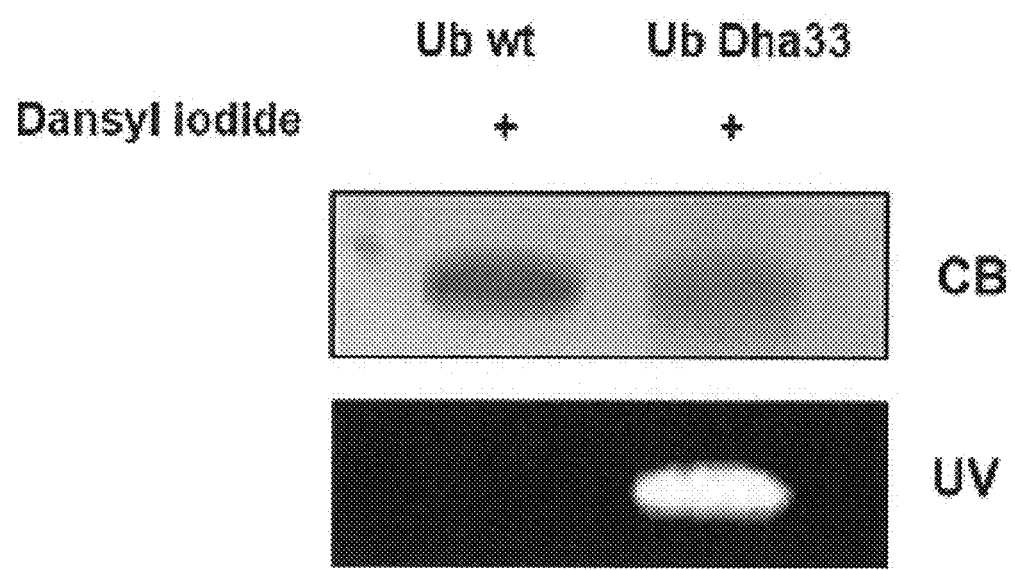
FIG. 8 shows the results obtained by coupling an alkyl iodide (13 in FIG. 4) to position 33 according to the method of the present invention and then confirming whether fluorescence is actually displayed.

In another example of the present invention, using the above-described method, in addition to PTM moieties, organic halogen compounds with diverse chemical groups ($4^{th}$ to $13^{th}$ compounds in FIG. 4), such as N-(3-iodopropyl) formamide, N-(3-iodopropyl)acetamide), 5-(dimethylamino)-N-(2-((3-iodopropyl)amino)ethyl)naphthalene-1-sulfonamide hydrochloride), iodobutane, 2-iodopropane, 2-iodo-2-methylpropane, 1-iodobutane, iodocyclopentane, 3-iodopropionic acid, and tert-butyl(4-iodobutoxy)dimethylsilane, were coupled to H3Dha79, UbDha33, or UbDha48 (FIG. 5, FIG. 6, FIG. 7). In particular, it was shown that the modified protein which was coupled with dansyl iodide (5-(dimethylamino)-N-(2-((3-iodopropyl)amino)ethyl) naphthalene-1-sulfonamide, $13^{th}$ compound in FIG. 4) emitted light at a UV wavelength of 365 nm, demonstrating a site-specific fluorescence labeling using the present method.

Therefore, in still another aspect, the present invention is directed to a method for producing a modified protein with diverse chemical groups at a site-specific position via new carbon-carbon bond formation, comprising the steps of: (a) incorporating phosphoserine (Sep) into a specific site in a target protein; (b) treating the phosphoserine-incorporated target protein with an alkali to convert the phosphoserine to dehydroalanine (Dha) to thereby activate the target protein; and (c) coupling the Dha with an organic halogen compound containing diverse chemical and functional groups including fluorescence by forming a carbon-carbon bond in the presence of a transition metal catalyst under optimized reaction condition, thereby obtaining a selectively modified protein with diverse chemical groups.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Synthesis of Alkyl Halides Modified at N-Terminus

Alkyl halides were synthesized in the following manner Because monomethylated iodides are easily cyclized to azetidines under alkaline conditions, Boc protection, Appel reaction and deprotection were sequentially applied to obtain monomethylated iodide hydrochloride salts. Dimethylated iodides were obtained by $S_N2$ reactions (including Finkelstein reaction) and halogen substitution reactions of alkyl chlorides. Because sodium iodide dissolves in acetone but sodium chloride does not dissolve therein, the reactions were performed such that products would be obtained by precipitation of undissolved salts. Trimethylated iodides were obtained by methylating dimethylamino propanol to prepare quaternary ammonium salts which were then heated in aqueous hydroiodic acid to obtain trimethyl amino propyl iodides.

1-1. Preparation of 3-Iodo-N-Methylpropan-1-Amine Hydrochloride, Monomethyl Iodides (1)

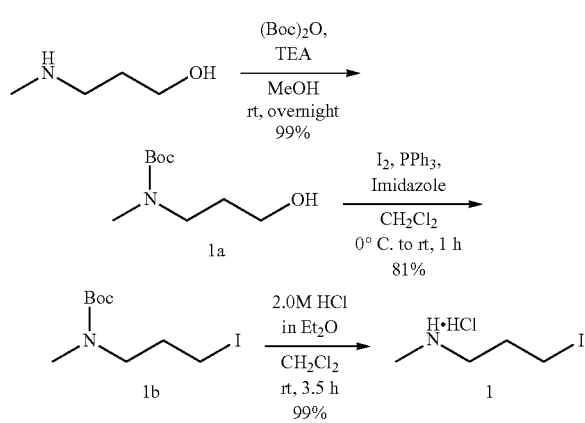

1) Preparation of tert-butyl (3-hydroxypropyl)(methyl)carbamate (1a)

At room temperature, triethylamine (TEA, 0.18 ml, 1.27 mmol) and 3-(methylamino)-1-propanol (0.10 ml, 1.06 mmol) in 3.50 ml of methanol were added to Boc anhydride (0.27 ml, 1.15 mmol). The mixture was stirred overnight, and then treated with $NaHCO_3$. The reaction mixture was diluted with EtOAc, and the organic layer was extracted three times with EtOAc (15 ml). The organic layer was dried over $MgSO_4$, filtered, and concentrated in vacuo. The mixture was separated by silica gel-based chromatography (EtOAc:hexane=1:1), thereby obtaining compound 1a (99%, 198 mg, 1.04 mmol).

The results were confirmed by $^1H$ NMR (600 MHz, $CDCl_3$), $^{13}C$ NMR (150 MHz, $CDCl_3$), and high-resolution MS (ESI).

2) Preparation of tert-butyl (3-iodopropyl)(methyl)carbamate (1b)

1.60 mL of a mixture of dichloromethane and $PPh_3$ (02.15 mg, 0.31 mmol) was placed on an ice batch, and then iodine (0.31 mmol, 75.6 mg), imidazole (0.47 mmol, 32.93 mg) and compound 1a (59.28 mg, 0.31 mmol) were added thereto at 5-minute intervals. After the ice batch was removed, the mixture was stirred for 1 hour, and then water was added to the mixture to stop the reaction. Then, the reaction mixture was diluted with $CH_2Cl_2$ (2 ml), and the organic layer was extracted three times with $CH_2Cl_2$ (10 ml). The organic layer was dried over $MgSO_4$, filtered, and concentrated in vacuo. The mixture was separated by silica gel-based chromatography (EtOAc:hexane=1:10), thereby obtaining compound 1b (81%, 76.04 mg, 0.25 mmol).

The results were confirmed by $^1H$ NMR (600 MHz, $CDCl_3$) and $^{13}C$ NMR (150 MHz, $CDCl_3$).

3) Preparation of 3-iodo-N-methylpropan-1-amine hydrochloride (1)

At room temperature, 2.0M hydrochloride in diethyl ether (0.50 ml) was added to a solution of compound 1b (61.20 mg, 0.21 mmol) in dichloromethane (1.00 ml). The mixture was stirred for 3.5 hours, and then concentrated in vacuo, thereby obtaining compound 1 (46.90 mg, 0.20 mmol, 99%) as a white solid.

The results were confirmed by $^1H$ NMR (600 MHz, $CDCl_3$), $^{13}C$ NMR (150 MHz, $CDCl_3$), and high-resolution MS (ESI).

1-2. Preparation of 3-iodo-N, N-dimethylpropan-1-amine hydrochloride, dimethyl iodides (2)

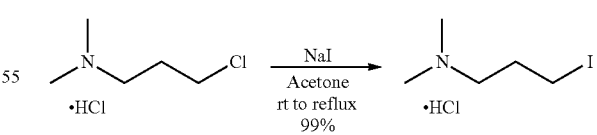

NaI (1.64 g, 10.92 mmol) was added to a solution of 3-(dimethylamino)-1-propyl chloride hydrochloride (863 mg, 5.46 mmol) in acetone, and then the solution was heated for 24 hours. The reaction solution was filtered, and then concentrated in vacuo to obtain compound 2 (2.7 g, 10.80 mmol, 99%).

The results were confirmed by $^1H$ NMR (600 MHz, $CDCl_3$): δ 3.27 (t, J=6.7 Hz, 1H), 3.22-3.15 (m, 1H), 2.87 (d, J=1.8 Hz, 5H), 2.23 (p, J=6.7 Hz, 1H) ppm; $^{13}$C NMR (150 MHz, CD3OD): δ 59.49, 43.66, 43.62, 29.37, 0.00 ppm; and High Resolution MS (ESI).

1-3. Preparation of 3-iodo-N,N,N-trimethylpropan-1-amine, trimethyl iodide (3)

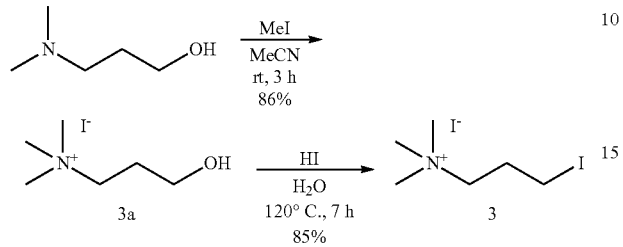

1) Preparation of 3-hydroxy-N,N,N-trimethylpropan-1-amine (3a)

A solution of 3-(dimethylamino)-1-propanol (70 μl, 0.97 mmol) in acetonitrile (3.20 ml) was treated with iodomethane (182 ul, 2.92 mmol) at 25° C. for 3 hours, and then treated with Et$_2$O. Non-aqueous quaternary ammonium salt was filtered, and the recrystallization was performed (EtOH: Et$_2$O=8:2), thereby obtaining compound 3a (205 mg, 0.84 mmol, 86%).

The results were confirmed by $^1$H NMR (600 MHz, CDCl$_3$), $^{13}$C NMR (150 MHz, CDCl$_3$), and high-resolution MS (ESI).

2) Preparation of 3-iodo-N,N,N-trimethylpropan-1-amine (3)

A solution of 3-N-trimethylamino-1-propanol (78.37 mg, 0.32 mmol) in water (1.6 ml) was treated with HI (57 wt % in H$_2$O, 1.6 mL) at 25° C. for 7 hours, and then heated to 120° C., and concentrated in vacuo, thereby obtaining compound 3 (113 mg, 0.08 mmol, 99%).

The results were confirmed by $^1$H NMR (600 MHz, CDCl$_3$), $^{13}$C NMR (150 MHz, CDCl$_3$), and high-resolution MS (ESI).

1-4. Preparation of N-(3-iodopropyl)formamide, formyl iodide (4)

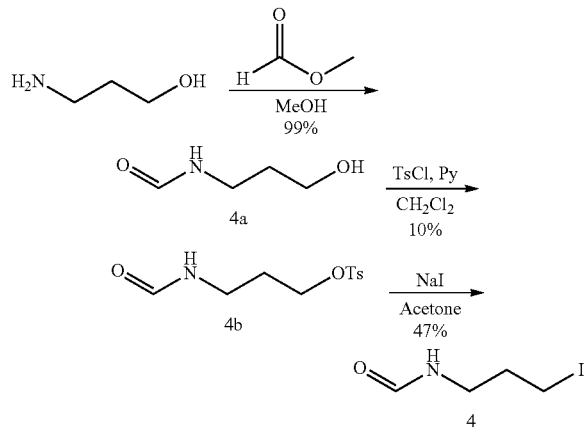

1) Preparation of N-(3-hydroxypropyl)formamide (4a)

Methyl formate (817.20 μl, 13.20 mmol) was added to a mixture of methanol (20 ml) and 3-aminopropan-1-ol (500 mg, 6.60 mmol) and allowed to react at 25° C. for 10 hours. The reaction solution was concentrated in vacuo, and then purified by flash column chromatography (DCM: MeOH=10:1) on silica gel, thereby obtaining N-(3-hydroxypropyl)formamide 4a (670 mg, 6.58 mmol, >99%).

The results were confirmed by $^1$H NMR (600 MHz, CDCl$_3$), $^{13}$C NMR (150 MHz, CDCl$_3$), and high-resolution MS (ESI).

2) Preparation of 3-formamidopropyl 4-methylbenzenesulfonate (4b)

P-toluenesulfonyl chloride (1.09 g, 5.70 mmol) and pyridine (0.55 ml, 6.84 mmol) were added to a mixture of dichloromethane (20 ml) and N-(3-hydroxypropyl)formamide 4a (590 mg, 5.70 mmol) and allowed to react at 25° C. Thereafter, the reaction solution was concentrated in vacuo, and then purified by flash column chromatography (only EtOAc) on silica gel, thereby obtaining compound 4b (147 mg, 0.57 mmol, 10%).

The results were confirmed by $^1$H NMR (600 MHz, CDCl$_3$), $^{13}$C NMR (150 MHz, CDCl$_3$), and high-resolution MS (ESI).

3) Preparation of N-(3-iodopropyl)formamide (4)

Sodium iodide (233 mg, 1.55 mmol) was added to a mixture of acetone (7 ml) and 3-formamidopropyl 4-methylbenzenesulfonate 4b (200 mg, 0.77 mmol) and allowed to react at 25° C. for 5 hours. Thereafter, the reaction solution was concentrated in vacuo, and then purified by flash column chromatography (only EtOAc) on silica gel, thereby obtaining compound 4 (77 mg, 0.36 mmol, 47%).

The results were confirmed by $^1$H NMR (600 MHz, CDCl$_3$), $^{13}$C NMR (150 MHz, CDCl$_3$), and high-resolution MS (ESI).

1-5. Preparation of N-(3-iodopropyl)acetamide, acetyl iodide (5)

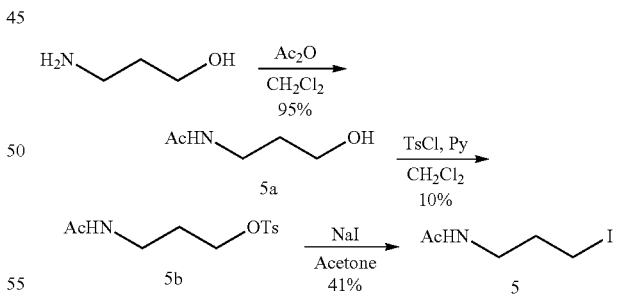

1) Preparation of N-(3-hydroxypropyl)acetamide (5a)

Acetic anhydride (673 μl, 6.60 mmol) was added to a mixture of dichloromethane (15 ml) and 3-aminopropan-1-ol (500 mg, 6.60 mmol) and allowed to react at 25° C. for 1 hour. Thereafter, the reaction solution was concentrated in vacuo, and then purified by flash column chromatography (DCM:MeOH=10:1) on silica gel, thereby obtaining N-(3-hydroxypropyl)acetamide 5a (735 mg, 6.58 mmol, 95%).

The results were confirmed by $^1$H NMR (600 MHz, CDCl$_3$), $^{13}$C NMR (150 MHz, CDCl$_3$), and high-resolution MS (ESI).

2) Preparation of 3-acetamidopropyl 4-methylbenzenesulfonate (5b)

P-toluenesulfonyl chloride (30 5 mg, 1.60 mmol) and pyridine (155.2 μl, 1.92 mmol) were added to a mixture of dichloromethane (5 ml) and N-(3-hydroxypropyl)acetamide 5a (187.9 mg, 1.60 mmol) and allowed to react at 25° C. for 4 hour. Thereafter, the reaction solution was concentrated in vacuo, and then purified by flash column chromatography (only EtOAc) on silica gel, thereby obtaining compound 5b (43 mg, 0.16 mmol, 10%).

The results were confirmed by $^1$H NMR (600 MHz, CDCl$_3$), $^{13}$C NMR (150 MHz, CDCl$_3$), and high-resolution MS (ESI).

3) Preparation of N-(3-iodopropyl)acetamide (5)

Sodium iodide (46.40 mg, 0.30 mmol) was added to a mixture of acetone (1 ml) and 3-acetamidopropyl 4-methylbenzenesulfonate 5b (43 mg, 0.16 mmol) and allowed to react at 25° C. for 4 hour. Thereafter, the reaction solution was concentrated in vacuo, and then purified by flash column chromatography (only EtOAc) on silica gel, thereby obtaining compound 5 (14 mg, 0.06 mmol, 41%).

The results were confirmed by $^1$H NMR (600 MHz, CDCl$_3$), $^{13}$C NMR (150 MHz, CDCl$_3$), and high-resolution MS (ESI).

1-6. Preparation of 5-(dimethylamino)-N-(2-((3-iodopropyl)amino)ethyl)naphthalene-1-sulfonamide hydrochloride (13)

1) Preparation of 5-(dimethylamino)-N-(2-hydroxyethyl)naphthalene-1-sulfonamide (13a)

Dansyl chloride (883.2 mg, 3.27 mmol, 1 equiv) and trimethylamine (455 μl, 3.27 mmol) were added to a mixture of dichloromethane (10 ml) and 2-aminoethanol (200 μl, 3.27 mmol) and allowed to react at 25° C. The reaction mixture was quenched with saturated NH$_4$Cl, and then extracted three times with CH$_2$Cl$_2$. The organic layer was dried with MgSO$_4$, concentrated in vacuo, and then purified by column chromatography on silica gel (EtOAc:hexane=1:1), thereby obtaining compound 13a (818.4 mg, 2.78 mmol, 85%).

The results were confirmed by $^1$H NMR (600 MHz, CDCl$_3$), $^{13}$C NMR (150 MHz, CDCl$_3$), and high-resolution MS (ESI).

2) Preparation of 2-(5-(dimethylamino)naphthalene-1-sulfonamido)ethyl 4-methylbenzenesulfonate (13b)

P-toluenesulfonyl chloride (518.5 mg, 2.72 mmol) and pyridine (0.29 ml, 3.54 mmol) were added to a mixture of dichloromethane (9 ml) and 5-(dimethylamino)-N-(2-hydroxyethyl)naphthalene-1-sulfonamide 13a (801.8 mg, 2.72 mmol) and allowed to react at 25° C. for 12 hours. The reaction mixture was quenched with saturated NH$_4$Cl, and then extracted three times with CH$_2$Cl$_2$. The organic layer was dried with MgSO$_4$, concentrated in vacuo, and then purified by column chromatography on silica gel (EtOAc:hexane=1:2), thereby obtaining compound 13b (792 mg, 1.77 mmol, 65%, recovered 13a=20%).

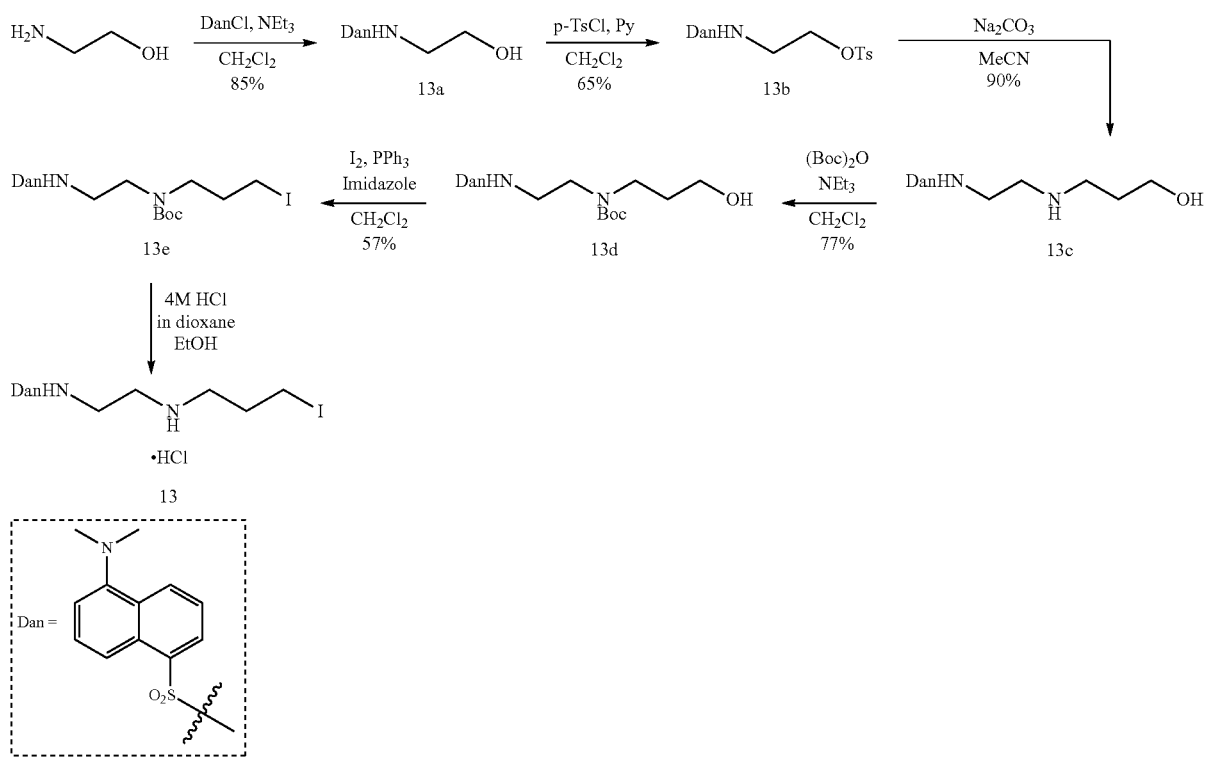

The results were confirmed by $^1$H NMR (600 MHz, CDCl$_3$), $^{13}$C NMR (150 MHz, CDCl$_3$), and high-resolution MS (ESI).

3) Preparation of 5-(dimethylamino)-N-(2-((3-hydroxypropyl)amino)ethyl)naphthalene-1-sulfonamide (13c)

3-aminopropanol (185.4 µl, 2.40 mmol) and sodium carbonate (254 mg, 2.40 mmol) were added to a mixture of acetonitrile (2.5 ml) and 2-(5-(dimethylamino)naphthalene-1-sulfonamido)ethyl 4-methylbenzenesulfonate 13b (362.17 mg, 0.80 mmol) and allowed to react at 65° C. for 10 hours. The reaction mixture was quenched with water, diluted with CH$_2$Cl$_2$, and then extracted three times with CH$_2$Cl$_2$. The organic layer was dried with MgSO$_4$, filtered, concentrated in vacuo, and then purified by column chromatography on silica gel (MC:MeOH=5:1), thereby obtaining compound 13c (253.1 mg, 0.72 mmol, 90%).

The results were confirmed by $^1$H NMR (600 MHz, CDCl$_3$), $^{13}$C NMR (150 MHz, CDCl$_3$), and high-resolution MS (ESI).

4) Preparation of tert-butyl (2-(5-(dimethylamino)naphthalene-1-sulfonamido)ethyl)(3-hydroxypropyl)carbamate (13d)

Boc anhydride (140 µl, 0.66 mmol) and triethylamine (92 µl, 0.66 mmol) were added to a mixture of acetonitrile (2.5 ml) and dichloromethane (6 ml) and 5-(dimethylamino)-N-(2-((3-hydroxypropyl)amino)ethyl)naphthalene-1-sulfonamide 13c (235 mg, 0.66 mmol) and allowed to react at 25° C. for 5 hours. The reaction mixture was quenched with saturated NH$_4$Cl, and then extracted three times with CH$_2$Cl$_2$. The organic layer was dried with MgSO$_4$, concentrated in vacuo, and then purified by column chromatography on silica gel (only EtOAc), thereby obtaining compound 13d (253.1 mg, 0.72 mmol, 90%).

The results were confirmed by $^1$H NMR (600 MHz, CDCl$_3$), $^{13}$C NMR (150 MHz, CDCl$_3$), and high-resolution MS (ESI).

5) Preparation of tert-butyl (2-(5-(dimethylamino)naphthalene-1-sulfonamido)ethyl)(3-iodopropyl)carbamate (13e)

Triphenylphosphine (131.1 mg, 0.5 mmol), imidazole (34.03 mg, 0.5 mmol) and iodine (126.9 mg, 0.5 mmol) were added to a solution of tert-butyl (2-(5-(dimethylamino)naphthalene-1-sulfonamido)ethyl)(3-hydroxypropyl) carbamate 13d in dichloromethane (5 ml) and allowed to react at 0° C. The reaction solution was incubated at 25° C. for 5 hours, after which it was diluted with diethyl ether and filtered through a celite pad to remove phosphine oxide. The filtrate was concentrated in vacuo, and then purified by column chromatography on silica gel (EtOAc:Hx=1:2), thereby obtaining compound 13e (158.7 mg, 0.28 mmol, 57%).

6) Preparation of 5-(dimethylamino)-N-(2-((3-iodopropyl)amino)ethyl)naphthalene-1-sulfonamide hydrochloride (13)

A solution of 4.0M hydrochloride in dioxane (0.7 ml) was added to a solution of tert-butyl (2-(5-(dimethylamino)naphthalene-1-sulfonamido)ethyl)(3-iodopropyl)carbamate 13e (158.7 mg, 0.28 mmol) in ethanol (1 ml) and allowed to react at 25° C. for 4 hours. The reaction solution was diluted with diethyl ether, filtered to remove undissolved ammonium salt, and then concentrated in vacuo, thereby obtaining compound 13 (130 mg, 0.26 mmol, 93%).

Example 2: Production of Sep-Containing Recombinant Protein

A pCDFDuetH3 wt vector was cloned from pCDFDue (Novagen) possessing *Xenopus laevis* histone H3 gene and C-terminal His6 tag between BamHI and AscI cleavage sites, thereby constructing wild-type histone H3 (H3 wt).

The pCDFDuet-H3 wt vector was subjected to nested PCR to insert TAG into the position of a codon coding for an amino acid at position 79, thereby constructing a pCDFDuet-H3K79TAG vector. The constructed vector was *E. coli* BL21(DE3) having a Sep incorporation system (pKD-SepRS9-EFSep21, pETDuet-SepRS9-sepT), and then expressed by a known method, thereby obtaining a protein.

The obtained protein was purified by Ni$^{2+}$-NTA agarose column chromatography, dialyzed in water with 3 mM β-mercaptoethanol, and then freeze-dried. If necessary, the histone protein obtained by the above-described method was further purified by reversed-phase HPLC.

Ubiquitin gene was inserted flanking the C-terminal His6-tag, and TAG was inserted into a position encoding an amino acid at position 33, thereby constructing a pCDFDuet-UB33TAG vector. The constructed vector was expressed in *E. coli*, thereby constructing a histone protein which was ubiquitylated and in which Sep was incorporated into position 33.

In the same manner, TAG was inserted into an amino acid at position 204 of the GFP gene having a C-terminal His6-tag, thereby constructing a pCDFDuet-GFP204TAG vector. The constructed vector was expressed in *E. coli*, and then purified in the same manner, thereby obtaining a protein.

Example 3: Activation of Sep-Labeled Protein by Treatment with Alkali

H3Sep79 (0.3 mg/ml) purified in Example 2 was reacted with varying concentrations of LiOH, Ba(OH)$_2$ or Sr(OH)$_2$ at room temperatures. 0.5 mM of dithiothreitol (DTT) was added in order to prevent the occurrence of oxidation reactions and side reactions. The reaction mixture was stirred for 30 minutes, neutralized with the same amount of acetic acid, and then dialyzed with distilled water overnight.

Protein in the reaction mixture was subjected to in-gel trypsin digestion, and then analyzed by MALDI-TOF MS. As a result, it could be seen that histone H3K79Sep was converted to dehydroalanine (Dha).

Example 4: Chemo-Selective Coupling of Alkyl Iodide and Dha-Containing Protein

For a coupling reaction, a stock solution of alkyl iodide was dissolved in distilled water, and then mixed with a solution containing a label-activated protein, and zinc powder was added thereto. The reaction mixture was incubated at room temperature for 30 minutes, and the supernatant was treated with bio-beads SM-2 (Bio-Rad) to remove the surfactant, and was dialyzed in water overnight.

4-1. Determination of pH Condition

According to a known method (19, 20), whether a metal-mediated coupling reaction of an organic compound can couple a post-translational modification (PTM) moiety to the protein was tested.

First, H3Dha79 (20 µM), an alkyl iodide (trimethyl iodide, 3 mM) and metals (0.1 mg zinc powder and 0.1 mM Cu(OAc)$_2$) were reacted in 20 µl of a reaction solution. As a result, it was shown that the protein was precipitated, indicating that no coupling occurred.

Next, buffer and surfactant (Triton X-100) were added, because the surfactant is known to be helpful in metal-based organic compound coupling that occurs in water. Reactions were performed at varying pHs (5.0 to 9.0) of various buffers (sodium citrate, sodium acetate, ammonium acetate, HEPES and potassium phosphate) including 0.1 wt % Triton X-100.

As a result, SDS-PAGE analysis indicated that a protein to which a modification was attached was more stable under acidic conditions, and Western blot analysis indicated that the protein was H3K79Me3. Additionally, the pH condition was further optimized, and as a result, it could be seen that a pH of 3.0 to 4.5 was an optimal condition in alkyl halide-based coupling reactions.

4-2. Investigation of Essential Factor for Metal-Based Coupling Reaction

Figure 9A:
FIG. 9A shows the results of examining carbon-carbon bond formation reaction conditions in the presence of various reaction buffers.
Figure 9B:
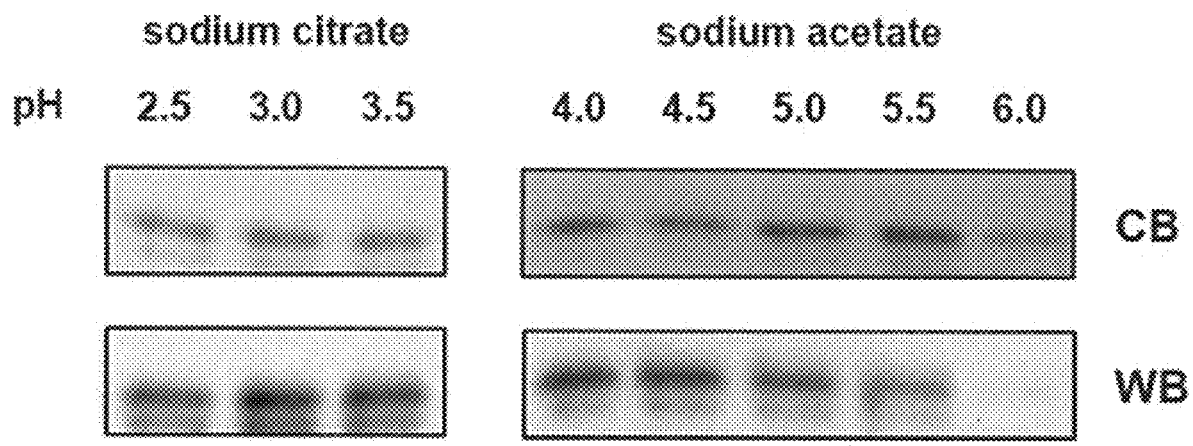
FIG. 9B shows the results of examining carbon-carbon bond formation reaction conditions at varying pHs of sodium citrate and sodium acetate, which showed reaction effects, among these reaction buffers.

Because it is important that a metal-based coupling reaction using a protein as a reactant is performed such that the function of the protein is not impaired, various kinds of buffers were tested. As a result, it could be seen that sodium acetate (pH 4.5) showed the best effect (FIGS. 9A-9B).

Figure 10A:
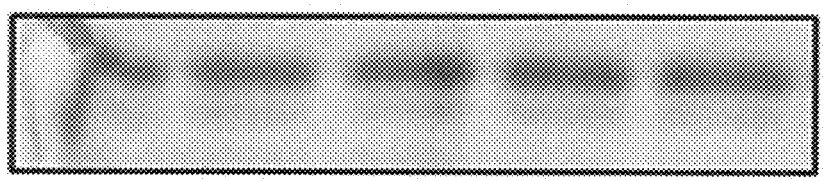
FIG. 10A and FIG. 10B show the results of examining carbon-carbon bond formation reaction conditions depending on the shape and amount of zinc (Zn) among transition metals.
Figure 10A:
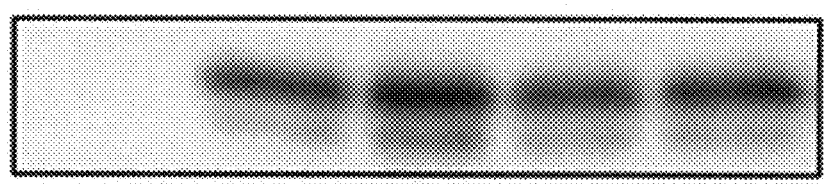
Figure 10B:
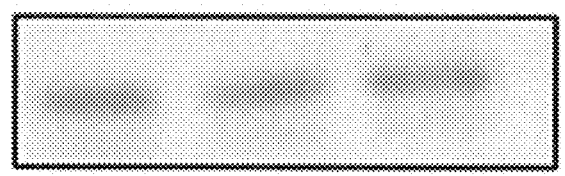
Figure 10B:
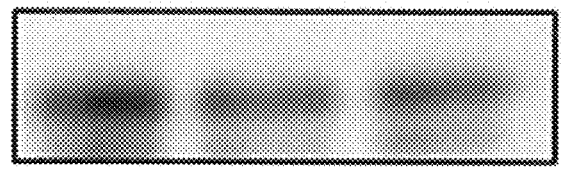
Figure 10C:
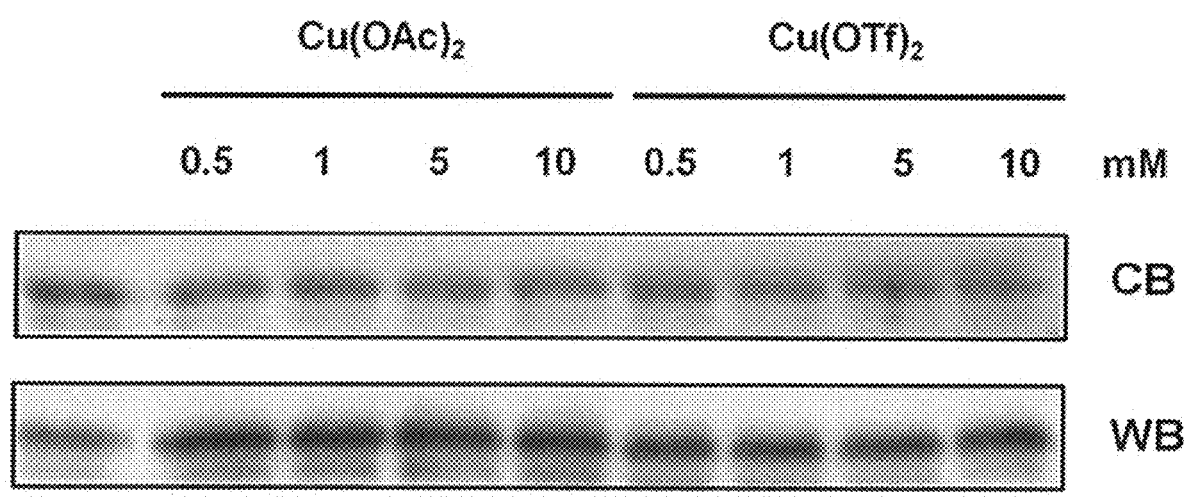
FIG. 10C shows the results of examining carbon-carbon bond formation reaction conditions depending on the shape and concentration of copper (Cu).

The concentration of zinc powder (0-1 mg in 20 µl reaction) was measured. As a result, it was shown that a concentration of 0.4 mg was optimal. Furthermore, materials having different particle sizes (zinc dust and zinc nanoparticles) were tested, and as a result, it could be seen that these materials had poor effects. For copper, 0-10 mM copper salt (Cu(OAc)$_2$ or Cu(OTf)$_2$) was tested, and as a result, it could be seen that, in the presence of 1 mM copper salt, the reaction sufficiently proceeded (FIGS. 10A-10C).

Figure 11A:
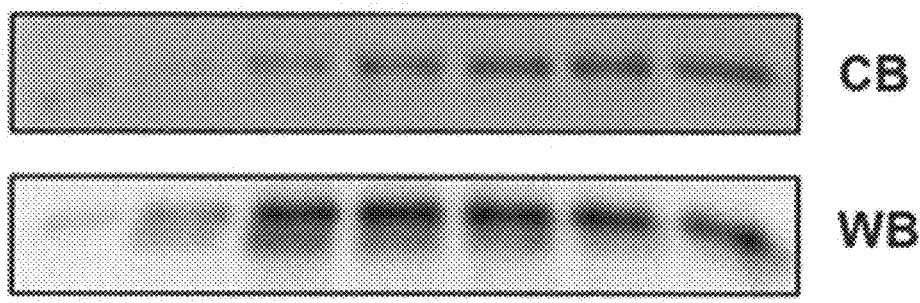
FIG. 11A shows the results of examining carbon-carbon bond formation reaction conditions at varying concentrations of surfactant Triton X-100.
Figure 11B:
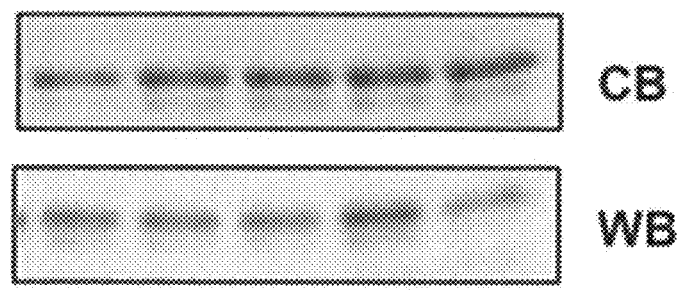
FIG. 11B shows the results of examining carbon-carbon bond formation reaction conditions at varying concentrations of TPGS (TOcopheryl polyethylene glycol succinate)
Figure 11C:
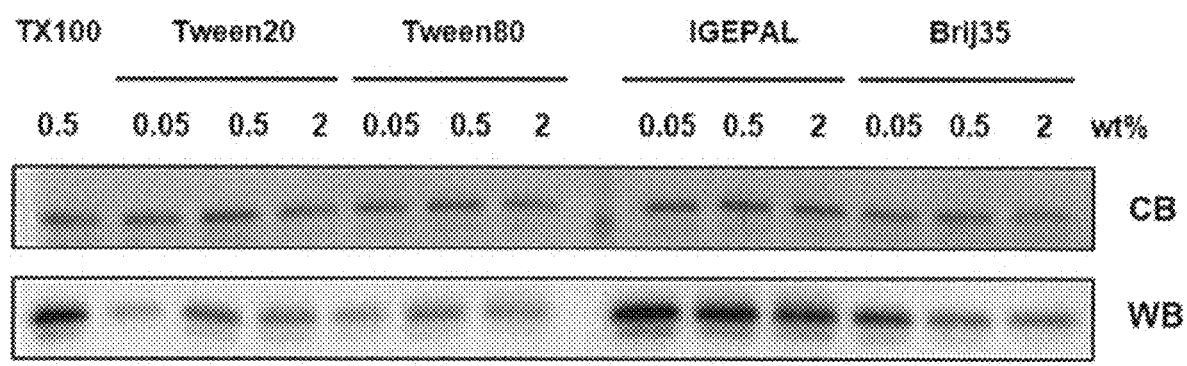
FIG. 11C the results of examining carbon-carbon bond formation reaction conditions at varying concentrations of various surfactants.

Because a radical is produced during this reaction, an intermediate needs to be stabilized using a proper surfactant. Thus, six kinds of surfactants (Triton X-100, TPGS, Tween 20, Tween 80, IGEPAL, and Brij35) were tested at a concentration of 0 to 5 wt %. As a result, it could be seen that Triton X-100 and IGEPAL exhibited optimal activity at a concentration of 2.0 wt % (FIGS. 11A-11C).

Figure 12:
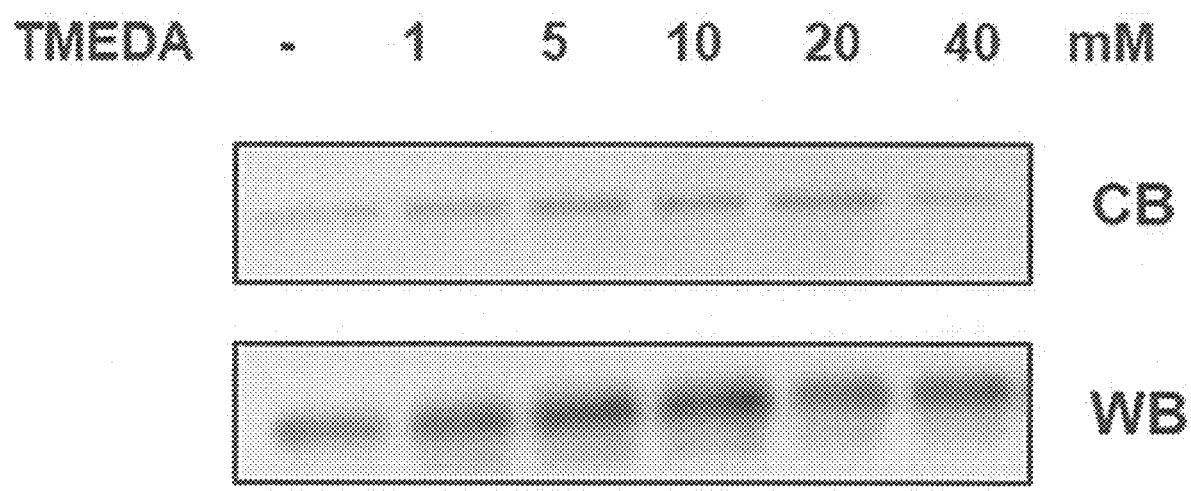
FIG. 12 shows the results of examining carbon-carbon bond formation reaction conditions at varying concentrations of TMEDA (tetramethylethylenediamine).
Figure 13A:
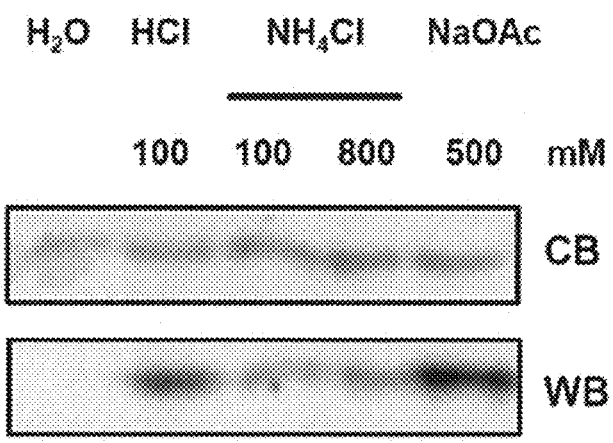
FIG. 13A shows the results of examining carbon-carbon bond formation reaction conditions on the kind and concentration of acid.
Figure 13B:
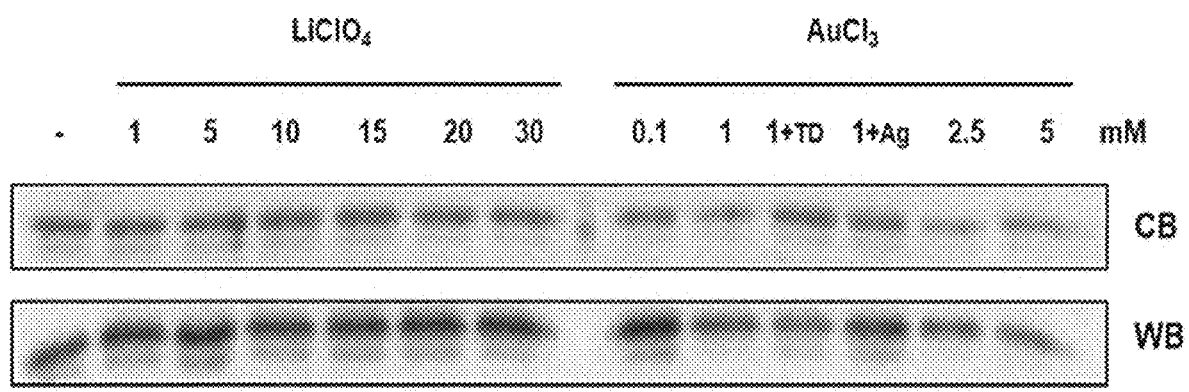
FIG. 13B shows the results of examining carbon-carbon bond formation reaction conditions on the kind and concentration of Lewis acid.

In addition, a material required to investigate the reaction was investigated, and as a result, it was shown that tetramethylethylenediamine (TMEDA) known to stabilize metal halide and free radical exhibited a reaction enhancing effect at a concentration of 10 mM (FIG. 12). Although silver salt (AgBF$_4$) mixed with acid (e.g., HCl and NH$_4$Cl) or Lewis acid (e.g., AuCl$_3$ and LiClO$_4$) is known to increase the efficiency of organic compound coupling, the reaction enhancing effect thereof was not observed in the reaction of the present invention (FIGS. 13A-13B).

Figure 14:
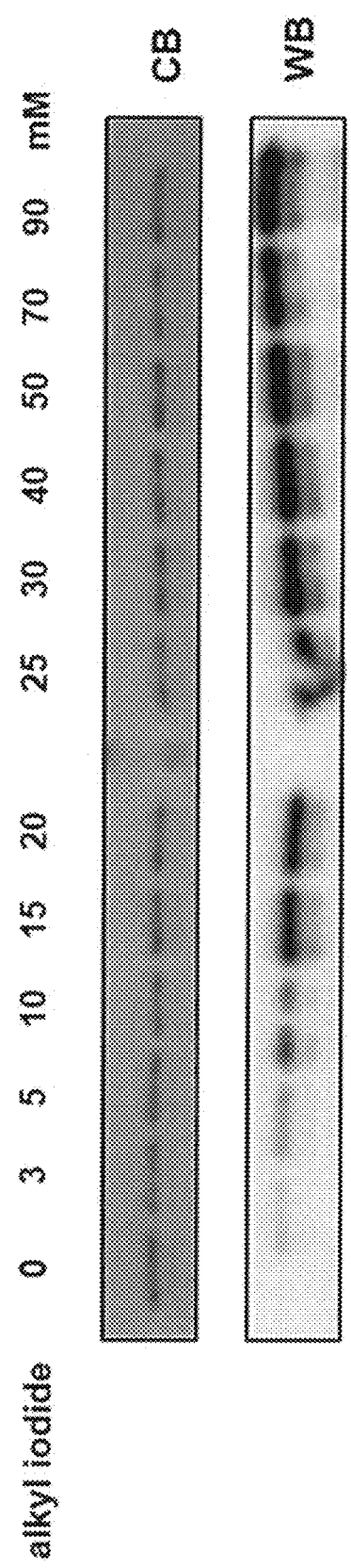
FIG. 14 shows the results of examining carbon-carbon bond formation reaction conditions at varying concentrations of an organic halogen compound.
Figure 15:
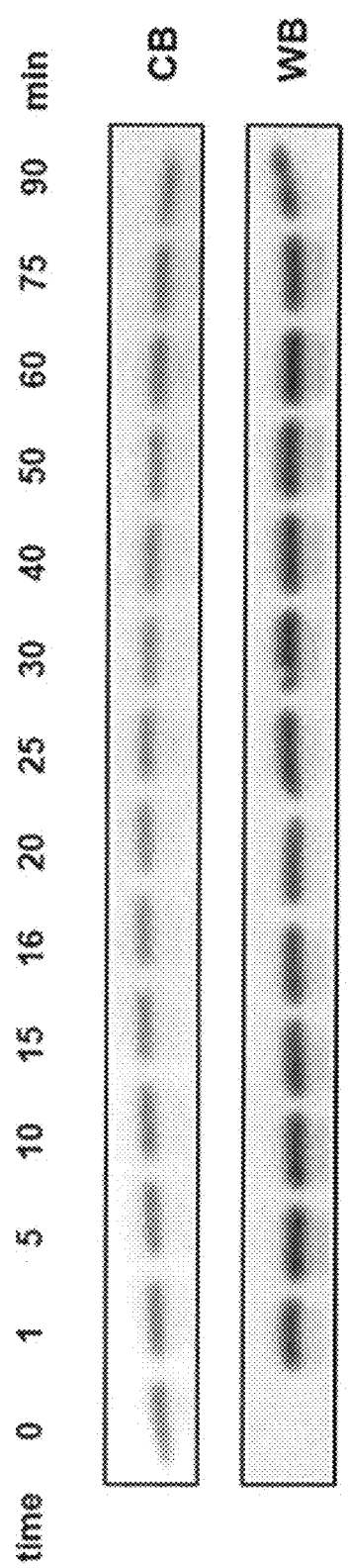
FIG. 15 shows analysis results as a function of carbon-carbon bond formation reaction time.

Finally, it was shown that organic halogen compound showed no enhancing effect at a concentration of 30 mM or more, and the coupling reaction was completed within 1 minute (FIGS. 14 and 15). The finally determined reaction conditions were as follows:

10 µM H3Dha78, 30 mM alkyl iodide, 0.4 mg Zn powder, 1 mM Cu(OAc)$_2$, 2.0 wt % Triton X-100 and 10 mM TMEDA were allowed to react in 500 mM sodium acetate buffer (pH 4.5) at room temperature.

To analyze the resulting products by Western blotting, the final reaction products were electrophoresed on 15% SDS-PAGE, and transferred to a nitrocellulose membrane, and analyzed using 1000-fold dilutions of anti-H3K79me1, anti-H3K79me2 and anti-H3K79me3 antibodies (Abcam). As a result, as shown in FIG. 2B, it could be seen that a methyl group was coupled to lysine at position 79 of histone H3 as desired.

Example 5: Mass Spectrometric Analysis of Protein

The molecular masses of histone H3 wt and modified histone H3 were measured using a MALDI-TOF mass spectrometer. A protein to be analyzed was mixed at a ratio of 1:1 with a reaction solution containing sinapinic acid, 0.1% TFA and 50% acetonitrile, and 1 µl of the mixture was sampled and dropped onto ground steel MTP384 for analysis.

The analysis instrument used was a Bruker Autoflex III MALDI-TOF mass spectrometer, and analysis mode was reflection mode. The molecular masses of the histones were further analyzed using linear positive ion mode.

For more accurate analysis, the target protein was digested by trypsin treatment, and then analyzed. For trypsin treatment, the target protein was electrophoresed on 15% SDS-PAGE, and then the protein band was cut out and treated with trypsin.

As a result, as shown in FIGS. 2A-2C and FIG. 5 to FIG. 7, it could be seen that a desired post-translational modification was attached to a desired site in histone.

Example 6: Histone Octamer Assembly and Chromatin Reconstitution

The same amount of freeze-dried histone proteins (H4, H2A, H2B and H3 wt, or H3K79me1, H3K79me2, H3K79me3) were added to unfolding buffer (8 M guanidium chloride in 20 mM NaOAC, pH 5.2 and 10 mM DTT) and stirred. Then, the protein solutions were dialyzed in refolding buffer (10 mM Tris-Hcl(pH7.5), 2M NaCl, 1 mM EDTA and 5 mM β-mercaptoethanol) at 4° C.

Histone octamers were isolated by Superdex 200 gel filtration and re-assembled using a PGEM-3z/601 plasmid. Using the histone octamers, a p53ML plasmid and ACF and NAPi proteins, chromatin was reconstructed.

Example 7: In Vitro Transcription Assay

Using the chromatin reconstructed in Example 6, an activator- and coactivator-dependent in vitro transcription assay was performed (21).

First, a chromatin template (8 µl, 40 ng DNA) including H3 wt or H3K79-methylated histone and a p53ML plasmid (having five p53 protein binding sites and containing a 390-nucleotide G-less cassette and an adenovirus major late promoter) was incubated with p53 protein (20 ng) in 0.5× HAT buffer (10 MM Hepes(pH7.8), 30 mM KCl, 2.5 mM DTT, 0.2 mM EDTA and 5 mM sodium butyrate) at 30° C. for 20 minutes in a total reaction volume of 20 µl.

The reaction solution was incubated with p300 protein (10 ng) and 20 µM acetyl-CoA at 30° C. for 30 minutes in a total reaction volume of 25 µl. Then, 5 µl HeLa nuclear extracts (0.1 mg/m), 1 µl DTT (250 mM), 2.5 µl 20×RB buffer (400 mM Hepes(pH 7.8), 120 mM MgCl$_2$) and BC200 buffer (20 mM Tris(pH7.9), 200 mM KCl, 0.2 mM EDTA and 20% glycerol) were added, and water was added such that the final KCl concentration would be 65 mM in a total reaction of 45.5 µl. The mixture was allowed to react at 30° C. for 20 minutes to thereby form a pre-initiation complex.

2.5 µl of a 20× nucleotide mix (10 mM ATP, CTP, 0.5 mM UTP, 2 mM 3'-O-methyl-GTP), 1 µl of [α-$^{32}$P]UTP (10 µCi/µl, 3000 Ci/mmol) and 1 µl of RNasin (10 U/µl) were added to the reaction mixture to adjust the total volume to 50 µl, and then transcription was performed at 30° C. for 50 minutes.

150 µl of stop buffer (150 mM sodium acetate(pH 5.2), 0.5% SDS, 10 mM EDTA) was added to the reaction mixture to stop the reaction, and then the reaction mixture was incubated with 30 µg of proteinase K at 37° C. for 30 minutes.

Finally, radio-labeled RNA was extracted with a solution of phenol/chloroform/isoamyl alcohol (25:24:1), and then precipitated with ethanol, after which it was separated on 5% polyacrylamide gel (19:1) containing 8M urea, and then analyzed by autoradiography.

Figure 3A:
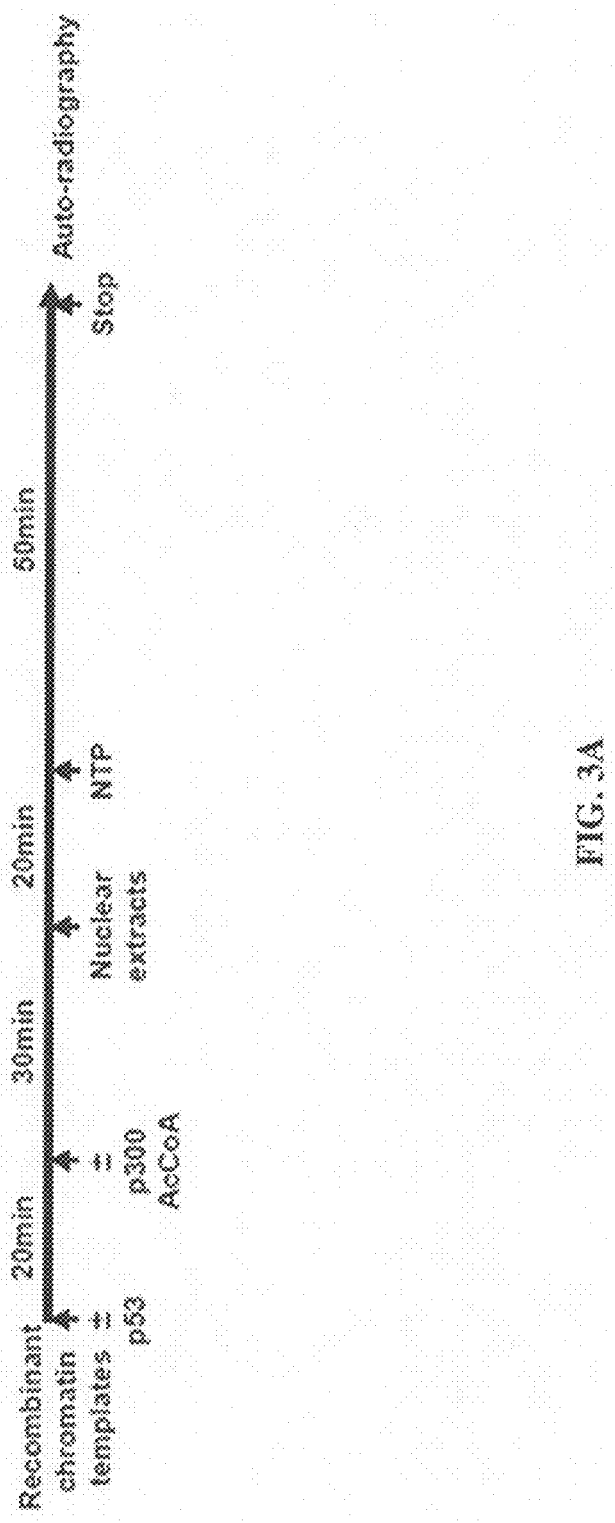
FIG. 3A is a schematic view showing an in vitro transcription assay performed in the present invention.
Figure 3B:
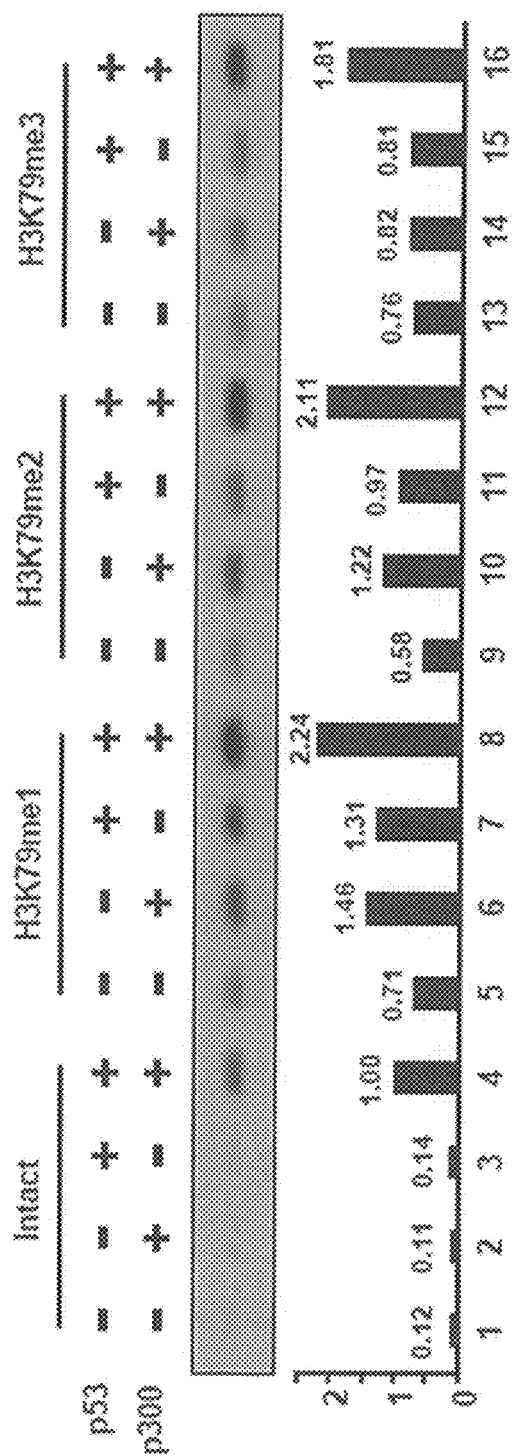
FIG. 3B shows the results of analyzing the effect of methylation of lysine at position 79 of histone H3 on chromatin transcription.
Figure 3C:
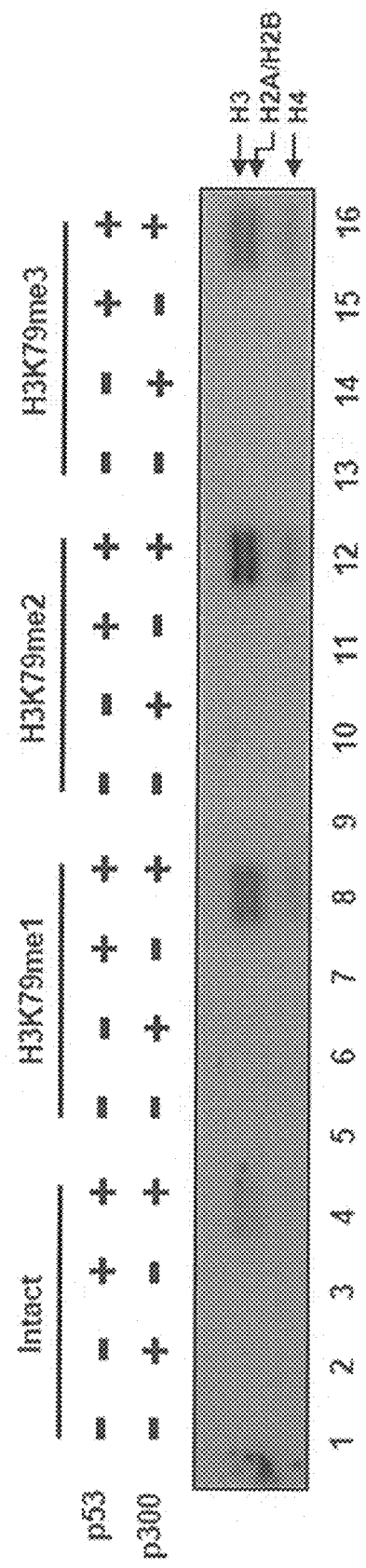
FIG. 3C shows the results of analyzing the effect of methylation of lysine at position 79 of histone H3 on p300-mediated chromatin acetylation.
Figure 3D:
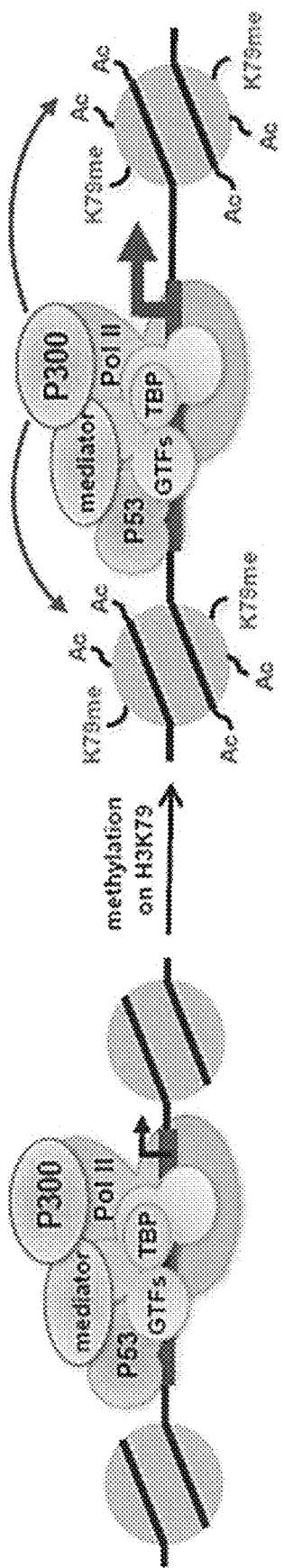
FIG. 3D is a schematic view showing transcriptional activation induced by methylation of lysine at position 79 of histone H3.

As a result, as can be seen in FIGS. 3A-3C, chromatin lacking methylation showed a low level of transcriptional activity, whereas methylated chromatin showed a high level of transcriptional activity (FIGS. 3B and 3C).

Example 8: In Vitro Acetyltransferase Activity Assay

The chromatin (35 µl, 350 ng DNA) reconstructed in Example 6 was incubated with p53 protein at 30° C. for 20 minutes, and then further incubated with p300 protein and 1 uCi³H-labelled acetyl-coenzyme A at 30° C. for 30 minutes in a total reaction volume of 40 pl. Then, the reaction product was electrophoresed on SDS-AGE, and then the acetylation activity was measured by autoradiography.

As a result, as shown in FIG. 3C, it could be seen that methylation of histone H3K79 increased p300-mediated histone acetylation.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The method for producing a site-specifically modified protein according to the present invention can incorporate desired diverse chemical groups including post-translational modification (PTM) moieties to a designated site in a target protein through a new carbon-carbon bond. Furthermore, the modified protein having a site-specific PTM thereto exhibits the same effect as that of a target protein present in cells. Thus, the present invention is useful for studies of cellular proteins, human diseases including cancers and neurodegenerative diseases, and new drug discovery, etc.

The invention claimed is:

1. A method for producing a site-specifically post-translational modification (PTM)-modified target protein, comprising the steps of:
   (a) incorporating phosphoserine (Sep) into a specific site in a target protein;
   (b) treating the phosphoserine-incorporated target protein with an alkali to convert the phosphoserine to dehydroalanine (Dha) to thereby activate the specific site; and
   (c) coupling the Dha-containing protein with an organic halogen compound containing various post-translational modification (PTM) moieties by forming a new carbon-carbon bond between the Dha and an alkyl halide in the presence of at least two transition metal catalyst selected from the group consisting of zinc, copper, iron, gold, silver, mercury, cobalt, manganese, and nickel under optimized reaction condition, thereby obtaining the site-specifically and authentically PTM-modified protein.

2. The method of claim 1, wherein the alkali is selected from the group consisting of lithium hydroxide (LiOH), barium hydroxide (Ba(OH)$_2$), strontium hydroxide (Sr(OH)$_2$), magnesium hydroxide (Mg(OH)$_2$), calcium hydroxide (Ca(OH)$_2$), radium hydroxide (Ra(OH)$_2$), and beryllium hydroxide (Be(OH)$_2$).

3. A method for producing a modified protein with diverse chemical groups, comprising the steps of:
   (a) incorporating phosphoserine (Sep) into a specific site in a target protein;
   (b) treating the phosphoserine-incorporated target protein with an alkali to convert the phosphoserine to dehydroalanine (Dha) to thereby activate the specific site; and
   (c) coupling the Dha-containing protein with an organic halogen compound containing various chemical groups by forming a new carbon-carbon bond between the Dha and an alkyl halide in the presence of at least two transition metal catalyst selected from the group consisting of zinc, copper, iron, gold, silver, mercury, cobalt, manganese, and nickel under optimized reaction condition, thereby obtaining the site-specifically modified protein.

4. The method of claim 3, wherein the organic halogen compound is 5-(dimethylamino)-N-(2-((3-iodopropyl)amino)ethyl)naphtalene-1-sulfonamide hydrochloride).

* * * * *